(12) United States Patent
Culbert et al.

(10) Patent No.: US 12,171,444 B2
(45) Date of Patent: Dec. 24, 2024

(54) SYSTEMS AND METHODS FOR REMOVAL OF BLOOD AND THROMBOTIC MATERIAL

(71) Applicant: WALK VASCULAR, LLC, Irvine, CA (US)

(72) Inventors: Bradley S. Culbert, Mission Viejo, CA (US); Thanh Van Nguyen, Westminster, CA (US); Caroline Kim, Signal Hill, CA (US)

(73) Assignee: Walk Vascular, LLC, Irvine, CA (US)

( * ) Notice: Subject to any disclaimer, the term of this patent is extended or adjusted under 35 U.S.C. 154(b) by 30 days.

(21) Appl. No.: 17/886,092

(22) Filed: Aug. 11, 2022

(65) Prior Publication Data

US 2022/0378450 A1    Dec. 1, 2022

Related U.S. Application Data

(63) Continuation of application No. 17/671,462, filed on Feb. 14, 2022.
(Continued)

(51) Int. Cl.
*A61B 17/22*    (2006.01)
*A61M 1/00*    (2006.01)
*A61M 39/22*    (2006.01)

(52) U.S. Cl.
CPC .............. *A61B 17/22* (2013.01); *A61M 1/73* (2021.05); *A61M 1/734* (2021.05); *A61M 1/743* (2021.05); *A61M 1/85* (2021.05); *A61M 39/227* (2013.01); *A61B 2017/22079* (2013.01); *A61M 2039/226* (2013.01); *A61M 2205/3331* (2013.01); *A61M 2210/12* (2013.01)

(58) Field of Classification Search
CPC ......... A61B 17/22; A61B 2017/22079; A61M 1/73; A61M 1/734; A61M 1/743; A61M 1/85; A61M 39/227; A61M 2039/226; A61M 2205/3331; A61M 2210/12
See application file for complete search history.

(56) References Cited

U.S. PATENT DOCUMENTS

| | | |
|---|---|---|
| 1,114,268 A | 10/1914 | Kells |
| 1,144,268 A | 6/1915 | Vickery |

(Continued)

FOREIGN PATENT DOCUMENTS

| | | |
|---|---|---|
| CN | 1120805 A | 4/1996 |
| CN | 201079629 Y | 7/2008 |

(Continued)

OTHER PUBLICATIONS

Angiojet Ultra Power Pulse Kit Information for Use, Medrad, Inc., downloaded from internet Jan. 23, 2017.
(Continued)

*Primary Examiner* — Susan S Su
*Assistant Examiner* — Ted Yang
(74) *Attorney, Agent, or Firm* — Workman Nydegger; Randy Shen

(57) ABSTRACT

An extension conduit for use with a system for aspirating thrombus includes a passageway extending between a distal end and a proximal end of the extension conduit, and a combined hydraulic and electrical control carried on the extension conduit and configured to be activated by a user to activate an electric switch while opening a valve to allow flow through the passageway.

27 Claims, 11 Drawing Sheets

Related U.S. Application Data

(60) Provisional application No. 63/149,623, filed on Feb. 15, 2021.

(56) References Cited

U.S. PATENT DOCUMENTS

| | | |
|---|---|---|
| 1,148,093 A | 7/1915 | Kells |
| 2,804,075 A | 8/1957 | Borden |
| 3,429,313 A | 2/1969 | Romanelli |
| 3,494,363 A | 2/1970 | Jackson |
| 3,589,363 A | 6/1971 | Banko et al. |
| 3,620,650 A | 11/1971 | Shaw |
| 3,631,847 A | 1/1972 | Hobbs |
| 3,693,613 A | 9/1972 | Kelman |
| 3,707,967 A | 1/1973 | Kitrilakis et al. |
| 3,748,435 A | 7/1973 | Reynolds |
| 3,807,401 A | 4/1974 | Bennett et al. |
| 3,818,913 A | 6/1974 | Wallach |
| 3,847,140 A | 11/1974 | Ayella |
| 3,916,892 A | 11/1975 | Hansen et al. |
| 3,918,453 A | 11/1975 | Leonard |
| 3,930,505 A | 1/1976 | Wallach |
| 3,955,573 A | 5/1976 | Hansen et al. |
| 4,030,503 A | 6/1977 | Clark, III |
| 4,274,411 A | 6/1981 | Dotson, Jr. |
| 4,299,221 A | 11/1981 | Phillips et al. |
| 4,465,470 A | 8/1984 | Kelman |
| 4,573,476 A | 3/1986 | Ruiz |
| 4,574,781 A | 3/1986 | Arkans |
| 4,638,539 A | 1/1987 | Palmer |
| 4,690,672 A | 9/1987 | Veltrup |
| 4,700,705 A | 10/1987 | Kensey et al. |
| 4,702,733 A | 10/1987 | Wright et al. |
| 4,715,853 A | 12/1987 | Prindle |
| 4,728,319 A | 3/1988 | Masch |
| 4,740,203 A | 4/1988 | Hoskins et al. |
| 4,747,821 A | 5/1988 | Kensey et al. |
| 4,747,834 A | 5/1988 | Prindle |
| 4,770,654 A | 9/1988 | Rogers et al. |
| 4,784,157 A | 11/1988 | Halls et al. |
| 4,790,813 A | 12/1988 | Kensey |
| 4,832,685 A | 5/1989 | Haines |
| 4,842,579 A | 6/1989 | Shiber |
| 4,854,325 A | 8/1989 | Stevens |
| 4,857,046 A | 8/1989 | Stevens et al. |
| 4,883,458 A | 11/1989 | Shiber |
| 4,883,467 A | 11/1989 | Franetzki et al. |
| 4,886,490 A | 12/1989 | Shiber |
| 4,886,507 A | 12/1989 | Patton et al. |
| 4,894,051 A | 1/1990 | Shiber |
| 4,898,574 A | 2/1990 | Uchiyama et al. |
| 4,957,482 A | 9/1990 | Shiber |
| 4,979,939 A | 12/1990 | Shiber |
| 4,998,919 A | 3/1991 | Schnepp-Pesch et al. |
| 5,002,553 A | 3/1991 | Shiber |
| 5,007,896 A | 4/1991 | Shiber |
| 5,011,468 A | 4/1991 | Lundquist et al. |
| 5,011,488 A | 4/1991 | Ginsburg |
| 5,024,651 A | 6/1991 | Shiber |
| 5,055,109 A | 10/1991 | Gould et al. |
| 5,057,098 A | 10/1991 | Zelman |
| 5,064,428 A | 11/1991 | Cope et al. |
| 5,073,164 A | 12/1991 | Hollister et al. |
| 5,073,168 A | 12/1991 | Danforth |
| 5,074,841 A | 12/1991 | Ademovic et al. |
| 5,078,722 A | 1/1992 | Stevens |
| 5,091,656 A | 2/1992 | Gahn |
| 5,125,893 A | 6/1992 | Dryden |
| 5,129,887 A | 7/1992 | Euteneuer et al. |
| 5,135,482 A | 8/1992 | Neracher |
| 5,135,531 A | 8/1992 | Shiber |
| 5,158,564 A | 10/1992 | Schnepp-Pesch et al. |
| 5,163,433 A | 11/1992 | Kagawa et al. |
| 5,195,954 A | 3/1993 | Schnepp-Pesch et al. |
| 5,197,795 A | 3/1993 | Mudrovich |
| 5,197,951 A | 3/1993 | Mahurkar |
| 5,234,407 A | 8/1993 | Teirstein et al. |
| 5,242,404 A | 9/1993 | Conley et al. |
| 5,243,997 A | 9/1993 | Uflacker et al. |
| 5,248,297 A | 9/1993 | Takase |
| 5,254,085 A | 10/1993 | Cleveland |
| 5,261,877 A | 11/1993 | Fine et al. |
| 5,284,486 A | 2/1994 | Kotula et al. |
| 5,290,247 A | 3/1994 | Crittenden |
| 5,306,244 A | 4/1994 | Shiber |
| 5,312,427 A | 5/1994 | Shturman |
| 5,318,518 A | 6/1994 | Plechinger et al. |
| 5,318,529 A | 6/1994 | Kontos |
| 5,320,604 A | 6/1994 | Walker et al. |
| 5,322,504 A | 6/1994 | Doherty et al. |
| 5,324,263 A | 6/1994 | Kraus et al. |
| 5,325,868 A | 7/1994 | Kimmelstiel |
| 5,327,906 A | 7/1994 | Fideler |
| 5,334,211 A | 8/1994 | Shiber |
| 5,342,293 A | 8/1994 | Zanger |
| 5,342,306 A | 8/1994 | Don Michael |
| 5,356,375 A | 10/1994 | Higley |
| 5,368,555 A | 11/1994 | Sussman et al. |
| 5,370,609 A | 12/1994 | Drasler et al. |
| 5,385,562 A | 1/1995 | Adams et al. |
| 5,389,072 A | 2/1995 | Imran |
| 5,392,778 A | 2/1995 | Horzewski |
| 5,395,315 A | 3/1995 | Griep |
| 5,403,274 A | 4/1995 | Cannon |
| 5,403,276 A | 4/1995 | Schechter et al. |
| 5,413,561 A | 5/1995 | Fischell et al. |
| 5,419,772 A | 5/1995 | Teitz et al. |
| 5,421,826 A | 6/1995 | Crocker et al. |
| 5,429,601 A | 7/1995 | Conley et al. |
| 5,443,078 A | 8/1995 | Uflacker |
| 5,443,443 A | 8/1995 | Shiber |
| 5,476,450 A | 12/1995 | Ruggio |
| 5,478,331 A | 12/1995 | Heflin et al. |
| 5,486,183 A | 1/1996 | Middleman et al. |
| 5,490,837 A | 2/1996 | Blaeser et al. |
| 5,496,267 A | 3/1996 | Drasler et al. |
| 5,507,738 A | 4/1996 | Ciervo |
| 5,524,180 A | 6/1996 | Wang et al. |
| 5,524,635 A | 6/1996 | Uflacker et al. |
| 5,527,274 A | 6/1996 | Zakko |
| 5,536,242 A | 7/1996 | Willard et al. |
| 5,538,002 A | 7/1996 | Boussignac et al. |
| 5,562,692 A | 10/1996 | Bair |
| 5,569,275 A | 10/1996 | Kotula et al. |
| 5,577,674 A | 11/1996 | Altonji et al. |
| 5,605,545 A | 2/1997 | Nowosielski et al. |
| 5,606,968 A | 3/1997 | Mang |
| 5,624,394 A | 4/1997 | Barnitz et al. |
| 5,626,563 A | 5/1997 | Dodge et al. |
| 5,634,475 A | 6/1997 | Wolvek |
| 5,647,847 A | 7/1997 | Lafontaine et al. |
| 5,653,696 A | 8/1997 | Shiber |
| 5,660,180 A | 8/1997 | Malinowski et al. |
| 5,669,876 A | 9/1997 | Schechter et al. |
| 5,695,507 A | 12/1997 | Auth et al. |
| 5,709,661 A | 1/1998 | Van et al. |
| 5,713,849 A | 2/1998 | Bosma et al. |
| 5,713,851 A | 2/1998 | Boudewijn et al. |
| 5,713,878 A | 2/1998 | Moutafis et al. |
| 5,730,717 A | 3/1998 | Gelbfish |
| 5,735,535 A | 4/1998 | Mccombs et al. |
| 5,766,191 A | 6/1998 | Trerotola |
| 5,772,674 A | 6/1998 | Nakhjavan |
| 5,785,685 A | 7/1998 | Kugler et al. |
| 5,795,322 A | 8/1998 | Boudewijn |
| 5,795,332 A | 8/1998 | Lucas et al. |
| 5,810,770 A | 9/1998 | Chin et al. |
| 5,827,229 A | 10/1998 | Auth et al. |
| 5,827,243 A | 10/1998 | Palestrant |
| 5,833,644 A | 11/1998 | Zadno-Azizi et al. |
| 5,843,022 A | 12/1998 | Willard et al. |
| 5,843,051 A | 12/1998 | Adams et al. |
| 5,853,384 A | 12/1998 | Bair |
| 5,855,567 A | 1/1999 | Reesemann |
| 5,868,702 A | 2/1999 | Stevens et al. |

(56) References Cited

U.S. PATENT DOCUMENTS

| | | |
|---|---|---|
| 5,871,462 A | 2/1999 | Yoder et al. |
| 5,876,414 A | 3/1999 | Straub |
| 5,885,238 A | 3/1999 | Stevens et al. |
| 5,885,244 A | 3/1999 | Leone et al. |
| 5,893,857 A | 4/1999 | Shturman et al. |
| 5,895,398 A | 4/1999 | Wensel et al. |
| 5,895,399 A | 4/1999 | Barbut et al. |
| 5,908,395 A | 6/1999 | Stalker et al. |
| 5,910,252 A | 6/1999 | Truitt et al. |
| 5,911,722 A | 6/1999 | Adler et al. |
| 5,916,192 A | 6/1999 | Nita et al. |
| 5,921,958 A | 7/1999 | Ressemann et al. |
| 5,938,645 A | 8/1999 | Gordon |
| 5,941,871 A | 8/1999 | Adams et al. |
| 5,944,686 A | 8/1999 | Patterson et al. |
| 5,957,901 A | 9/1999 | Mottola et al. |
| 5,989,210 A | 11/1999 | Morris et al. |
| 5,989,271 A | 11/1999 | Bonnette et al. |
| 6,001,112 A | 12/1999 | Taylor |
| 6,007,513 A | 12/1999 | Anis et al. |
| 6,019,728 A | 2/2000 | Iwata et al. |
| 6,022,336 A | 2/2000 | Zadno-Azizi et al. |
| 6,027,460 A | 2/2000 | Shturman |
| 6,039,078 A * | 3/2000 | Tamari .............. A61M 1/74  604/6.11 |
| 6,080,170 A | 6/2000 | Nash et al. |
| 6,090,118 A | 7/2000 | Mcguckin, Jr. |
| 6,096,001 A | 8/2000 | Drasler et al. |
| 6,101,406 A | 8/2000 | Hacker et al. |
| 6,126,635 A | 10/2000 | Simpson et al. |
| 6,129,697 A | 10/2000 | Drasler et al. |
| 6,129,698 A | 10/2000 | Beck |
| 6,146,355 A | 11/2000 | Biggs |
| 6,146,396 A | 11/2000 | Konya et al. |
| 6,152,909 A | 11/2000 | Bagaoisan et al. |
| 6,156,046 A | 12/2000 | Passafaro et al. |
| 6,159,230 A | 12/2000 | Samuels |
| 6,165,188 A | 12/2000 | Saadat et al. |
| 6,176,844 B1 | 1/2001 | Lee |
| 6,179,809 B1 | 1/2001 | Khairkhahan et al. |
| 6,179,851 B1 | 1/2001 | Barbut et al. |
| 6,183,432 B1 | 2/2001 | Milo |
| 6,190,357 B1 | 2/2001 | Ferrari et al. |
| 6,196,989 B1 | 3/2001 | Padget et al. |
| 6,206,898 B1 | 3/2001 | Honeycutt et al. |
| 6,216,573 B1 | 4/2001 | Moutafis et al. |
| 6,224,570 B1 | 5/2001 | Le et al. |
| 6,224,585 B1 | 5/2001 | Pfeiffer |
| 6,238,405 B1 | 5/2001 | Findlay et al. |
| 6,258,061 B1 | 7/2001 | Drasler et al. |
| 6,283,719 B1 | 9/2001 | Frantz et al. |
| 6,293,960 B1 | 9/2001 | Ken |
| 6,331,171 B1 | 12/2001 | Cohen |
| 6,348,040 B1 | 2/2002 | Stalker et al. |
| 6,375,635 B1 | 4/2002 | Moutafis et al. |
| 6,423,032 B2 | 7/2002 | Parodi |
| 6,440,148 B1 | 8/2002 | Shiber |
| 6,454,741 B1 | 9/2002 | Muni et al. |
| 6,454,775 B1 | 9/2002 | Demarais et al. |
| 6,471,683 B2 | 10/2002 | Drasler et al. |
| 6,481,439 B1 | 11/2002 | Lewis et al. |
| 6,488,672 B1 | 12/2002 | Dance et al. |
| 6,508,823 B1 | 1/2003 | Gonon |
| 6,511,454 B1 | 1/2003 | Nakao et al. |
| 6,533,772 B1 | 3/2003 | Sherts et al. |
| 6,544,209 B1 | 4/2003 | Drasler et al. |
| 6,544,231 B1 | 4/2003 | Palmer et al. |
| 6,551,302 B1 | 4/2003 | Rosinko et al. |
| 6,554,794 B1 | 4/2003 | Mueller et al. |
| 6,554,799 B1 | 4/2003 | Hatamura et al. |
| 6,558,366 B1 | 5/2003 | Drasler et al. |
| 6,558,401 B1 | 5/2003 | Azizi |
| 6,569,147 B1 | 5/2003 | Evans et al. |
| 6,569,148 B2 | 5/2003 | Bagaoisan et al. |
| 6,572,578 B1 | 6/2003 | Blanchard |
| 6,579,270 B2 | 6/2003 | Sussman et al. |
| 6,585,705 B1 | 7/2003 | Maginot et al. |
| 6,599,271 B1 | 7/2003 | Easley |
| 6,615,835 B1 | 9/2003 | Cise et al. |
| 6,616,679 B1 | 9/2003 | Khosravi et al. |
| 6,622,367 B1 | 9/2003 | Bolduc et al. |
| 6,623,495 B2 | 9/2003 | Findlay et al. |
| 6,635,034 B1 | 10/2003 | Cosmescu |
| 6,635,070 B2 | 10/2003 | Leeflang et al. |
| 6,638,235 B2 | 10/2003 | Miller et al. |
| 6,652,546 B1 | 11/2003 | Nash et al. |
| 6,652,548 B2 | 11/2003 | Evans et al. |
| 6,663,613 B1 | 12/2003 | Evans et al. |
| 6,669,710 B2 | 12/2003 | Moutafis et al. |
| 6,676,637 B1 | 1/2004 | Bonnette et al. |
| 6,702,830 B1 | 3/2004 | Demarais et al. |
| 6,719,717 B1 | 4/2004 | Johnson et al. |
| 6,723,081 B1 | 4/2004 | Hektner |
| 6,726,675 B1 | 4/2004 | Beyar |
| 6,752,800 B1 | 6/2004 | Winston et al. |
| 6,755,803 B1 | 6/2004 | Le et al. |
| 6,755,812 B2 | 6/2004 | Peterson et al. |
| 6,790,215 B2 | 9/2004 | Findlay et al. |
| 6,805,684 B2 | 10/2004 | Bonnette et al. |
| 6,818,001 B2 | 11/2004 | Wulfman et al. |
| 6,824,545 B2 | 11/2004 | Sepetka et al. |
| 6,824,550 B1 | 11/2004 | Noriega et al. |
| 6,830,577 B2 | 12/2004 | Nash et al. |
| 6,875,193 B1 | 4/2005 | Bonnette et al. |
| 6,899,712 B2 | 5/2005 | Moutafis et al. |
| 6,926,726 B2 | 8/2005 | Drasler et al. |
| 6,929,633 B2 | 8/2005 | Evans et al. |
| 6,936,056 B2 | 8/2005 | Nash et al. |
| 6,945,977 B2 | 9/2005 | Demarais et al. |
| 6,958,059 B2 | 10/2005 | Zadno-Azizi |
| 6,984,239 B1 | 1/2006 | Drasler et al. |
| 6,986,778 B2 | 1/2006 | Zadno-Azizi |
| 6,991,625 B1 | 1/2006 | Gately et al. |
| 7,008,434 B2 | 3/2006 | Kurz et al. |
| 7,044,958 B2 | 5/2006 | Douk et al. |
| 7,108,704 B2 | 9/2006 | Trerotola |
| 7,122,017 B2 | 10/2006 | Moutafis et al. |
| 7,220,269 B1 | 5/2007 | Ansel et al. |
| 7,232,452 B2 | 6/2007 | Adams et al. |
| 7,374,560 B2 | 5/2008 | Ressemann et al. |
| 7,431,711 B2 | 10/2008 | Moutafis et al. |
| 7,479,147 B2 | 1/2009 | Honeycutt et al. |
| 7,481,222 B2 | 1/2009 | Reissmann |
| 7,588,033 B2 | 9/2009 | Wondka |
| 7,591,816 B2 | 9/2009 | Wang et al. |
| 7,604,612 B2 | 10/2009 | Ressemann et al. |
| 7,615,042 B2 | 11/2009 | Beyar et al. |
| 7,621,886 B2 | 11/2009 | Burnett |
| 7,654,996 B2 | 2/2010 | Lynn |
| 7,655,016 B2 | 2/2010 | Demarais et al. |
| 7,666,161 B2 | 2/2010 | Nash et al. |
| 7,699,804 B2 | 4/2010 | Barry et al. |
| 7,713,235 B2 | 5/2010 | Torrance et al. |
| 7,717,685 B2 | 5/2010 | Moutafis et al. |
| 7,717,898 B2 | 5/2010 | Gately et al. |
| 7,736,355 B2 | 6/2010 | Itou et al. |
| 7,753,868 B2 | 7/2010 | Hoffa |
| 7,753,880 B2 | 7/2010 | Malackowski |
| 7,766,894 B2 | 8/2010 | Weitzner et al. |
| 7,776,005 B2 | 8/2010 | Haggstrom et al. |
| 7,798,996 B1 | 9/2010 | Haddad et al. |
| 7,798,999 B2 | 9/2010 | Bailey et al. |
| 7,806,864 B2 | 10/2010 | Haddad et al. |
| 7,833,239 B2 | 11/2010 | Nash |
| 7,842,055 B2 | 11/2010 | Pintor et al. |
| 7,846,175 B2 | 12/2010 | Bonnette et al. |
| 7,862,575 B2 | 1/2011 | Tal |
| 7,867,192 B2 | 1/2011 | Bowman et al. |
| 7,875,004 B2 | 1/2011 | Yodfat et al. |
| 7,879,022 B2 | 2/2011 | Bonnette et al. |
| 7,887,510 B2 | 2/2011 | Karpowicz et al. |
| 7,905,710 B2 | 3/2011 | Wang et al. |
| 7,909,801 B2 | 3/2011 | Hinchliffe |
| 7,909,810 B2 | 3/2011 | Noone |

(56) References Cited

U.S. PATENT DOCUMENTS

| | | | |
|---|---|---|---|
| 7,914,482 B2 | 3/2011 | Urich et al. |
| 7,914,549 B2 | 3/2011 | Morsi |
| 7,918,654 B2 | 4/2011 | Adahan |
| 7,918,822 B2 | 4/2011 | Kumar et al. |
| 7,918,835 B2 | 4/2011 | Callahan et al. |
| 7,935,077 B2 | 5/2011 | Thor et al. |
| 7,951,073 B2 | 5/2011 | Freed |
| 7,951,107 B2 | 5/2011 | Staid et al. |
| 7,951,112 B2 | 5/2011 | Patzer |
| 7,959,603 B2 | 6/2011 | Wahr et al. |
| 7,959,608 B2 | 6/2011 | Nash et al. |
| 7,976,528 B2 | 7/2011 | Nash et al. |
| 7,981,128 B2 | 7/2011 | To et al. |
| 7,981,129 B2 | 7/2011 | Nash et al. |
| 7,998,114 B2 | 8/2011 | Lombardi |
| 8,007,490 B2 | 8/2011 | Schaeffer et al. |
| 8,012,766 B2 | 9/2011 | Graham |
| 8,021,351 B2 | 9/2011 | Boldenow et al. |
| 8,034,018 B2 | 10/2011 | Lutwyche |
| 8,043,312 B2 | 10/2011 | Noriega et al. |
| 8,043,313 B2 | 10/2011 | Krolik et al. |
| 8,062,246 B2 | 11/2011 | Moutafis et al. |
| 8,062,257 B2 | 11/2011 | Moberg et al. |
| 8,065,096 B2 | 11/2011 | Moberg et al. |
| 8,066,677 B2 | 11/2011 | Lunn et al. |
| 8,070,694 B2 | 12/2011 | Galdonik et al. |
| 8,075,546 B2 | 12/2011 | Carlisle et al. |
| 8,092,483 B2 | 1/2012 | Galdonik et al. |
| 8,123,777 B2 | 2/2012 | Krolik et al. |
| 8,140,146 B2 | 3/2012 | Kim et al. |
| 8,142,458 B2 | 3/2012 | Shturman |
| 8,152,782 B2 | 4/2012 | Jang et al. |
| 8,152,951 B2 | 4/2012 | Zawacki et al. |
| 8,157,787 B2 | 4/2012 | Nash et al. |
| 8,162,877 B2 | 4/2012 | Bonnette et al. |
| 8,162,966 B2 | 4/2012 | Connor et al. |
| 8,177,739 B2 | 5/2012 | Cartledge et al. |
| 8,182,462 B2 | 5/2012 | Istoc et al. |
| 8,187,228 B2 | 5/2012 | Bikovsky |
| 8,187,229 B2 | 5/2012 | Weitzner et al. |
| 8,202,243 B2 | 6/2012 | Morgan |
| 8,209,060 B2 | 6/2012 | Ledford |
| 8,221,348 B2 | 7/2012 | Hackett et al. |
| 8,226,673 B2 | 7/2012 | Nash et al. |
| 8,246,573 B2 | 8/2012 | Ali et al. |
| 8,246,580 B2 | 8/2012 | Hopkins et al. |
| 8,257,298 B2 | 9/2012 | Hamboly |
| 8,257,343 B2 | 9/2012 | Chan et al. |
| 8,262,645 B2 | 9/2012 | Bagwell et al. |
| 8,267,893 B2 | 9/2012 | Moberg et al. |
| 8,287,485 B2 | 10/2012 | Kimura et al. |
| 8,291,337 B2 | 10/2012 | Gannin et al. |
| 8,292,841 B2 | 10/2012 | Gregersen |
| 8,308,745 B2 | 11/2012 | Seto et al. |
| 8,317,739 B2 | 11/2012 | Christoph |
| 8,317,770 B2 | 11/2012 | Miesel et al. |
| 8,317,773 B2 | 11/2012 | Appling et al. |
| 8,317,786 B2 | 11/2012 | Dahla et al. |
| 8,323,239 B2 | 12/2012 | Bednarek et al. |
| 8,323,268 B2 | 12/2012 | Ring et al. |
| 8,337,175 B2 | 12/2012 | Dion et al. |
| 8,337,451 B2 | 12/2012 | Lareau et al. |
| 8,343,097 B2 | 1/2013 | Pile-Spellman et al. |
| 8,343,131 B2 | 1/2013 | Vinten-Johansen |
| 8,348,896 B2 | 1/2013 | Wagner |
| 8,353,858 B2 | 1/2013 | Kozak et al. |
| 8,353,860 B2 | 1/2013 | Boulais et al. |
| 8,357,138 B2 | 1/2013 | Pierpont et al. |
| 8,372,038 B2 | 2/2013 | Urich et al. |
| 8,394,078 B2 | 3/2013 | Torrance et al. |
| 8,398,579 B2 | 3/2013 | Morris et al. |
| 8,398,581 B2 | 3/2013 | Panotopoulos |
| 8,398,582 B2 | 3/2013 | Gordon et al. |
| 8,414,521 B2 | 4/2013 | Baker et al. |
| 8,414,522 B2 | 4/2013 | Kamen et al. |
| 8,414,943 B2 | 4/2013 | Wijngaarden et al. |
| 8,419,709 B2 | 4/2013 | Haddad et al. |
| 8,425,458 B2 | 4/2013 | Scopton |
| 8,430,837 B2 | 4/2013 | Jenson et al. |
| 8,430,845 B2 | 4/2013 | Wahr et al. |
| 8,430,861 B2 | 4/2013 | Schwartz et al. |
| 8,439,876 B2 | 5/2013 | Spohn et al. |
| 8,454,557 B1 | 6/2013 | Qi et al. |
| 8,465,456 B2 | 6/2013 | Stivland |
| 8,465,867 B2 | 6/2013 | Kim |
| 8,483,980 B2 | 7/2013 | Moberg et al. |
| 8,491,523 B2 | 7/2013 | Thor et al. |
| 8,500,697 B2 | 8/2013 | Kurth et al. |
| 8,506,537 B2 | 8/2013 | Torstensen et al. |
| 8,523,801 B2 | 9/2013 | Nash et al. |
| 8,529,498 B2 | 9/2013 | Moutafis et al. |
| 8,545,432 B2 | 10/2013 | Renati et al. |
| 8,545,514 B2 | 10/2013 | Ferrera |
| 8,562,555 B2 | 10/2013 | Macmahon et al. |
| 8,579,926 B2 | 11/2013 | Pintor et al. |
| 8,597,238 B2 | 12/2013 | Bonnette et al. |
| 8,608,699 B2 | 12/2013 | Blomquist |
| 8,613,618 B2 | 12/2013 | Brokx |
| 8,613,724 B2 | 12/2013 | Lanier et al. |
| 8,617,110 B2 | 12/2013 | Moberg et al. |
| 8,617,127 B2 | 12/2013 | Woolston et al. |
| 8,623,039 B2 | 1/2014 | Seto et al. |
| 8,628,549 B2 | 1/2014 | To et al. |
| 8,641,671 B2 | 2/2014 | Michaud et al. |
| 8,647,294 B2 | 2/2014 | Bonnette et al. |
| 8,652,086 B2 | 2/2014 | Gerg et al. |
| 8,657,777 B2 | 2/2014 | Kozak et al. |
| 8,657,785 B2 | 2/2014 | Torrance et al. |
| 8,663,259 B2 | 3/2014 | Levine et al. |
| 8,668,464 B2 | 3/2014 | Kensy et al. |
| 8,668,665 B2 | 3/2014 | Gerg et al. |
| 8,670,836 B2 | 3/2014 | Aeschlimann et al. |
| 8,672,876 B2 | 3/2014 | Jacobson et al. |
| 8,681,010 B2 | 3/2014 | Moberg et al. |
| 8,715,237 B2 | 5/2014 | Moberg et al. |
| 8,721,674 B2 | 5/2014 | Kusleika |
| 8,758,325 B2 | 6/2014 | Webster et al. |
| 8,758,364 B2 | 6/2014 | Eckhouse et al. |
| 8,783,151 B1 | 7/2014 | Janardhan et al. |
| 8,803,030 B1 | 8/2014 | Janardhan et al. |
| 8,814,892 B2 | 8/2014 | Galdonik et al. |
| 8,851,866 B2 | 10/2014 | Moutafis et al. |
| 8,852,219 B2 | 10/2014 | Wulfman et al. |
| 8,864,792 B2 | 10/2014 | Eckhouse et al. |
| 8,888,801 B2 | 11/2014 | To et al. |
| 8,900,179 B2 | 12/2014 | Jenson et al. |
| 8,900,214 B2 | 12/2014 | Nance et al. |
| 8,920,402 B2 | 12/2014 | Nash et al. |
| 8,932,320 B1 | 1/2015 | Janardhan et al. |
| 8,932,321 B1 | 1/2015 | Janardhan et al. |
| 8,936,447 B2 | 1/2015 | Abal |
| 8,945,030 B2 | 2/2015 | Weston |
| 8,962,561 B2 | 2/2015 | Shalgi et al. |
| 8,970,384 B2 | 3/2015 | Yodfat et al. |
| 8,974,418 B2 | 3/2015 | Bonnette et al. |
| 8,979,798 B2 | 3/2015 | Shener et al. |
| 8,986,241 B2 | 3/2015 | Evans et al. |
| 8,986,252 B2 | 3/2015 | Cummings et al. |
| 8,998,843 B2 | 4/2015 | Bonnette et al. |
| 9,005,237 B2 | 4/2015 | Eckhouse et al. |
| 9,011,114 B2 | 4/2015 | Farrell et al. |
| 9,017,294 B2 | 4/2015 | Mcguckin et al. |
| 9,023,070 B2 | 5/2015 | Levine et al. |
| 9,024,768 B2 | 5/2015 | Mandro et al. |
| 9,033,925 B2 | 5/2015 | Moberg et al. |
| 9,034,008 B2 | 5/2015 | Eckhouse et al. |
| 9,042,938 B2 | 5/2015 | Nimbalker et al. |
| 9,078,691 B2 | 7/2015 | Morris et al. |
| 9,113,955 B2 | 8/2015 | Noriega et al. |
| 9,119,941 B2 | 9/2015 | Rollins et al. |
| 9,119,942 B1 | 9/2015 | Rollins et al. |
| 9,198,679 B2 | 12/2015 | To et al. |
| 9,238,122 B2 | 1/2016 | Malhi et al. |
| 9,248,221 B2 | 2/2016 | Look et al. |

(56) References Cited

U.S. PATENT DOCUMENTS

| | | |
|---|---|---|
| 9,254,144 B2 | 2/2016 | Nguyen et al. |
| 9,278,189 B2 | 3/2016 | Corbett |
| 9,282,992 B2 | 3/2016 | Levine et al. |
| 9,283,040 B2 | 3/2016 | Hendrick et al. |
| 9,308,016 B2 | 4/2016 | Escudero et al. |
| 9,314,263 B2 | 4/2016 | Escudero et al. |
| 9,332,999 B2 | 5/2016 | Ray et al. |
| 9,333,007 B2 | 5/2016 | Escudero et al. |
| 9,358,035 B2 | 6/2016 | Kojima |
| 9,402,938 B2 | 8/2016 | Aklog et al. |
| 9,433,427 B2 | 9/2016 | Look et al. |
| 9,456,872 B2 | 10/2016 | Hendrick et al. |
| 9,474,543 B2 | 10/2016 | Mcguckin et al. |
| 9,492,192 B2 | 11/2016 | To et al. |
| 9,492,193 B2 | 11/2016 | To et al. |
| 9,510,854 B2 | 12/2016 | Mallaby |
| 9,586,023 B2 | 3/2017 | Bonnette et al. |
| 9,592,073 B2 | 3/2017 | Kojima et al. |
| 9,597,480 B2 | 3/2017 | Purdy et al. |
| 9,693,789 B2 | 7/2017 | Garrison et al. |
| 9,700,346 B2 | 7/2017 | Levine et al. |
| 9,770,551 B1 | 9/2017 | Faden |
| 9,782,195 B2 | 10/2017 | Mactaggart et al. |
| 9,795,406 B2 | 10/2017 | Levine et al. |
| 9,808,266 B2 | 11/2017 | Ray et al. |
| 9,827,404 B2 | 11/2017 | Nance et al. |
| 9,833,257 B2 | 12/2017 | Bonnette et al. |
| 9,883,877 B2 | 2/2018 | Look et al. |
| 10,238,853 B2 | 3/2019 | Kume et al. |
| 10,314,608 B2 | 6/2019 | Jenson et al. |
| 10,383,983 B2 | 8/2019 | Aklog et al. |
| 10,390,926 B2 | 8/2019 | Janardhan et al. |
| 10,426,885 B2 | 10/2019 | Criado et al. |
| 10,492,805 B2 | 12/2019 | Culbert et al. |
| 10,499,944 B2 | 12/2019 | Mallaby |
| 10,531,883 B1 | 1/2020 | Deville et al. |
| 10,702,292 B2 | 7/2020 | Look et al. |
| 10,716,880 B2 | 7/2020 | Culbert et al. |
| 11,490,909 B2 | 11/2022 | Look et al. |
| 11,497,521 B2 | 11/2022 | Mallaby |
| 11,653,945 B2 | 5/2023 | Jenson et al. |
| 11,672,561 B2 | 6/2023 | Look et al. |
| 11,678,905 B2 | 6/2023 | Look et al. |
| 2001/0004700 A1 | 6/2001 | Honeycutt et al. |
| 2001/0051811 A1 | 12/2001 | Bonnette et al. |
| 2002/0016564 A1 | 2/2002 | Courtney et al. |
| 2002/0029052 A1 | 3/2002 | Evans et al. |
| 2002/0058904 A1 | 5/2002 | Boock et al. |
| 2002/0068895 A1 | 6/2002 | Beck |
| 2002/0133114 A1 | 9/2002 | Toh et al. |
| 2002/0138095 A1 | 9/2002 | Mazzocchi et al. |
| 2002/0165575 A1 | 11/2002 | Saleh |
| 2002/0173812 A1 | 11/2002 | Mcguckin et al. |
| 2002/0173819 A1 | 11/2002 | Leeflang et al. |
| 2002/0176788 A1 | 11/2002 | Moutafis et al. |
| 2002/0177789 A1 | 11/2002 | Ferry et al. |
| 2003/0032918 A1 | 2/2003 | Quinn |
| 2003/0040694 A1 | 2/2003 | Dorros et al. |
| 2003/0055404 A1 | 3/2003 | Moutafis |
| 2003/0069549 A1 | 4/2003 | Macmahon et al. |
| 2003/0083681 A1 | 5/2003 | Moutafis et al. |
| 2003/0088187 A1 | 5/2003 | Saadat et al. |
| 2003/0088209 A1 | 5/2003 | Chiu et al. |
| 2003/0139751 A1 | 7/2003 | Evans et al. |
| 2003/0144688 A1 | 7/2003 | Brady et al. |
| 2003/0216760 A1 | 11/2003 | Welch et al. |
| 2003/0220556 A1 | 11/2003 | Porat et al. |
| 2003/0236533 A1 | 12/2003 | Wilson et al. |
| 2004/0030281 A1 | 2/2004 | Goble et al. |
| 2004/0049149 A1 | 3/2004 | Drasler et al. |
| 2004/0049225 A1 | 3/2004 | Denison |
| 2004/0054322 A1 | 3/2004 | Vargas |
| 2004/0082915 A1 | 4/2004 | Kadan |
| 2004/0087988 A1 | 5/2004 | Heitzmann et al. |
| 2004/0097829 A1 | 5/2004 | Mcrury et al. |
| 2004/0143225 A1 | 7/2004 | Callan et al. |
| 2004/0147871 A1 | 7/2004 | Burnett |
| 2004/0153109 A1 | 8/2004 | Tiedtke et al. |
| 2004/0158136 A1 | 8/2004 | Gough et al. |
| 2004/0167463 A1 | 8/2004 | Zawacki et al. |
| 2004/0193046 A1 | 9/2004 | Nash et al. |
| 2004/0199201 A1 | 10/2004 | Kellett et al. |
| 2004/0215222 A1 | 10/2004 | Krivoruchko |
| 2004/0236214 A1 | 11/2004 | Opie et al. |
| 2004/0243157 A1 | 12/2004 | Connor et al. |
| 2005/0004594 A1 | 1/2005 | Nool et al. |
| 2005/0043682 A1 | 2/2005 | Kucklick et al. |
| 2005/0049547 A1 | 3/2005 | Anspach et al. |
| 2005/0065426 A1 | 3/2005 | Porat et al. |
| 2005/0085769 A1* | 4/2005 | MacMahon ............ A61M 1/81 604/96.01 |
| 2005/0102165 A1 | 5/2005 | Oshita et al. |
| 2005/0159716 A1 | 7/2005 | Kobayashi et al. |
| 2005/0196748 A1 | 9/2005 | Ericson |
| 2005/0238503 A1 | 10/2005 | Rush et al. |
| 2005/0240116 A1 | 10/2005 | Saadat et al. |
| 2005/0240120 A1 | 10/2005 | Modesitt |
| 2005/0240146 A1 | 10/2005 | Nash et al. |
| 2005/0244521 A1 | 11/2005 | Strickland et al. |
| 2005/0256457 A1 | 11/2005 | Rome |
| 2005/0277851 A1 | 12/2005 | Whittaker et al. |
| 2005/0283150 A1 | 12/2005 | Moutafis et al. |
| 2006/0009785 A1 | 1/2006 | Maitland et al. |
| 2006/0041245 A1 | 2/2006 | Ferry et al. |
| 2006/0058836 A1 | 3/2006 | Bose et al. |
| 2006/0063973 A1 | 3/2006 | Makower et al. |
| 2006/0064051 A1 | 3/2006 | Gross |
| 2006/0064123 A1 | 3/2006 | Bonnette et al. |
| 2006/0074442 A1 | 4/2006 | Noriega et al. |
| 2006/0093989 A1 | 5/2006 | Hahn et al. |
| 2006/0142630 A1 | 6/2006 | Meretei |
| 2006/0149191 A1 | 7/2006 | DiFiore |
| 2006/0184186 A1 | 8/2006 | Noone |
| 2006/0212055 A1 | 9/2006 | Karabey et al. |
| 2006/0229550 A1 | 10/2006 | Staid et al. |
| 2006/0229587 A1 | 10/2006 | Beyar et al. |
| 2006/0264808 A1 | 11/2006 | Staid et al. |
| 2006/0282150 A1 | 12/2006 | Olson et al. |
| 2007/0016105 A1 | 1/2007 | Mamourian |
| 2007/0060879 A1 | 3/2007 | Weitzner et al. |
| 2007/0073233 A1* | 3/2007 | Thor ............... A61M 25/0122 606/167 |
| 2007/0073268 A1 | 3/2007 | Goble et al. |
| 2007/0078438 A1 | 4/2007 | Okada |
| 2007/0118165 A1 | 5/2007 | Demello et al. |
| 2007/0135812 A1 | 6/2007 | Sartor |
| 2007/0167804 A1 | 7/2007 | Park et al. |
| 2007/0197956 A1 | 8/2007 | Le et al. |
| 2007/0197963 A1 | 8/2007 | Griffiths et al. |
| 2007/0219467 A1 | 9/2007 | Clark et al. |
| 2007/0225615 A1 | 9/2007 | Chechelski et al. |
| 2007/0225739 A1 | 9/2007 | Pintor et al. |
| 2007/0239182 A1 | 10/2007 | Glines et al. |
| 2007/0249990 A1 | 10/2007 | Cosmescu |
| 2007/0270755 A1 | 11/2007 | Von et al. |
| 2007/0299306 A1 | 12/2007 | Parasher et al. |
| 2008/0009784 A1 | 1/2008 | Leedle et al. |
| 2008/0091061 A1 | 4/2008 | Kumar et al. |
| 2008/0097339 A1 | 4/2008 | Ranchod et al. |
| 2008/0097465 A1 | 4/2008 | Rollins et al. |
| 2008/0097563 A1 | 4/2008 | Petrie et al. |
| 2008/0108960 A1 | 5/2008 | Shapland et al. |
| 2008/0119824 A1 | 5/2008 | Weitzner et al. |
| 2008/0125698 A1 | 5/2008 | Gerg et al. |
| 2008/0125798 A1 | 5/2008 | Osborne et al. |
| 2008/0195058 A1 | 8/2008 | Moutafis et al. |
| 2008/0195139 A1 | 8/2008 | Donald et al. |
| 2008/0243054 A1 | 10/2008 | Mollstam et al. |
| 2008/0243153 A1 | 10/2008 | Nguyen et al. |
| 2008/0249501 A1 | 10/2008 | Yamasaki |
| 2008/0255539 A1 | 10/2008 | Booth |
| 2008/0255596 A1 | 10/2008 | Jenson et al. |
| 2008/0294008 A1 | 11/2008 | Toyama |
| 2008/0294181 A1 | 11/2008 | Wensel et al. |

(56) References Cited

U.S. PATENT DOCUMENTS

| | | | |
|---|---|---|---|
| 2008/0306465 A1 | 12/2008 | Bailey et al. |
| 2008/0319376 A1 | 12/2008 | Wilcox et al. |
| 2009/0018566 A1 | 1/2009 | Escudero et al. |
| 2009/0048607 A1 | 2/2009 | Rockley |
| 2009/0054825 A1 | 2/2009 | Melsheimer et al. |
| 2009/0082722 A1 | 3/2009 | Munger et al. |
| 2009/0105645 A1 | 4/2009 | Kidd et al. |
| 2009/0105690 A1 | 4/2009 | Schaeffer et al. |
| 2009/0157057 A1 | 6/2009 | Ferren et al. |
| 2009/0198172 A1 | 8/2009 | Garrison et al. |
| 2009/0264940 A1 | 10/2009 | Beale et al. |
| 2009/0292212 A1 | 11/2009 | Ferren et al. |
| 2009/0306476 A1 | 12/2009 | Banik et al. |
| 2009/0306692 A1 | 12/2009 | Barrington et al. |
| 2010/0010524 A1 | 1/2010 | Barrington et al. |
| 2010/0030134 A1 | 2/2010 | Fitzgerald et al. |
| 2010/0030186 A1 | 2/2010 | Stivland |
| 2010/0094201 A1 | 4/2010 | Mallaby |
| 2010/0145302 A1 | 6/2010 | Cull et al. |
| 2010/0160851 A1 | 6/2010 | Dimalanta et al. |
| 2010/0174233 A1 | 7/2010 | Kuban et al. |
| 2010/0191178 A1 | 7/2010 | Ross et al. |
| 2010/0204613 A1 | 8/2010 | Rollins et al. |
| 2010/0204672 A1 | 8/2010 | Lockhart et al. |
| 2010/0217275 A1 | 8/2010 | Carmeli et al. |
| 2010/0217276 A1 | 8/2010 | Garrison et al. |
| 2010/0228273 A1 | 9/2010 | Staid et al. |
| 2010/0268236 A1 | 10/2010 | Moutafis et al. |
| 2010/0274191 A1 | 10/2010 | Ting |
| 2010/0280534 A1 | 11/2010 | Sher |
| 2011/0034986 A1 | 2/2011 | Chou et al. |
| 2011/0040314 A1 | 2/2011 | Mcguckin, Jr. et al. |
| 2011/0091331 A1 | 4/2011 | Moutafis et al. |
| 2011/0092892 A1 | 4/2011 | Nitsan et al. |
| 2011/0106019 A1 | 5/2011 | Bagwell et al. |
| 2011/0152920 A1 | 6/2011 | Eckhouse et al. |
| 2011/0160683 A1 | 6/2011 | Pinotti et al. |
| 2011/0282426 A1 | 11/2011 | Mitra et al. |
| 2012/0053557 A1 | 3/2012 | Abal |
| 2012/0059340 A1 | 3/2012 | Larsson |
| 2012/0059354 A1 | 3/2012 | Zarate |
| 2012/0065656 A1 | 3/2012 | Karwei |
| 2012/0065660 A1 | 3/2012 | Ferrera et al. |
| 2012/0071907 A1 | 3/2012 | Pintor et al. |
| 2012/0078080 A1 | 3/2012 | Foley et al. |
| 2012/0123509 A1 | 5/2012 | Merrill et al. |
| 2012/0130415 A1 | 5/2012 | Tal et al. |
| 2012/0165756 A1 | 6/2012 | Root et al. |
| 2012/0239008 A1 | 9/2012 | Fojtik |
| 2012/0239064 A1 | 9/2012 | Cartier et al. |
| 2012/0239066 A1 | 9/2012 | Levine et al. |
| 2012/0259265 A1 | 10/2012 | Salehi et al. |
| 2012/0277665 A1 | 11/2012 | Tachoire et al. |
| 2012/0277698 A1 | 11/2012 | Andrew et al. |
| 2012/0289910 A1 | 11/2012 | Shtul et al. |
| 2012/0291811 A1 | 11/2012 | Dabney et al. |
| 2012/0330196 A1 | 12/2012 | Nita |
| 2013/0085381 A1 | 4/2013 | Comerota et al. |
| 2013/0184734 A1 | 7/2013 | Morris et al. |
| 2013/0190701 A1 | 7/2013 | Kirn |
| 2013/0218186 A1 | 8/2013 | Dubois et al. |
| 2013/0245543 A1 | 9/2013 | Gerg et al. |
| 2013/0267891 A1 | 10/2013 | Malhi et al. |
| 2013/0281788 A1 | 10/2013 | Garrison |
| 2013/0310809 A1 | 11/2013 | Armstrong et al. |
| 2013/0310845 A1 | 11/2013 | Thor et al. |
| 2013/0331776 A1 | 12/2013 | Klein et al. |
| 2014/0005699 A1 | 1/2014 | Bonnette et al. |
| 2014/0058361 A1 | 2/2014 | Gordon |
| 2014/0142594 A1 | 5/2014 | Fojtik |
| 2014/0147246 A1 | 5/2014 | Chappel et al. |
| 2014/0148830 A1 | 5/2014 | Bowman |
| 2014/0155931 A1 | 6/2014 | Bose et al. |
| 2014/0228569 A1 | 8/2014 | Okumura et al. |
| 2014/0228869 A1 | 8/2014 | Bonnette et al. |
| 2014/0257097 A1 | 9/2014 | Bonnette et al. |
| 2014/0276920 A1 | 9/2014 | Hendrick et al. |
| 2014/0309589 A1 | 10/2014 | Momose et al. |
| 2014/0323906 A1 | 10/2014 | Peatfield et al. |
| 2014/0360494 A1* | 12/2014 | Herskovic ............ A61M 11/007 128/200.26 |
| 2014/0378951 A1 | 12/2014 | Dye |
| 2015/0025446 A1 | 1/2015 | Jacobson et al. |
| 2015/0032138 A1 | 1/2015 | Jenson et al. |
| 2015/0094673 A1 | 4/2015 | Pratt et al. |
| 2015/0094748 A1 | 4/2015 | Nash et al. |
| 2015/0142030 A1 | 5/2015 | Mactaggart et al. |
| 2015/0257724 A1 | 9/2015 | Lautenschläger |
| 2015/0283309 A1 | 10/2015 | Look et al. |
| 2015/0305765 A1 | 10/2015 | Fojtik et al. |
| 2015/0306286 A1 | 10/2015 | Ross et al. |
| 2015/0327875 A1 | 11/2015 | Look et al. |
| 2015/0343182 A1* | 12/2015 | Vazales .............. A61M 16/0463 604/267 |
| 2015/0374391 A1 | 12/2015 | Quick et al. |
| 2016/0051263 A1 | 2/2016 | Stigall et al. |
| 2016/0058614 A1* | 3/2016 | Ross ........................ A61F 9/007 606/107 |
| 2016/0143721 A1 | 5/2016 | Rosenbluth et al. |
| 2016/0220741 A1 | 8/2016 | Garrison et al. |
| 2016/0331645 A1 | 11/2016 | Bagwell et al. |
| 2017/0065396 A1 | 3/2017 | Ook et al. |
| 2017/0079672 A1 | 3/2017 | Quick |
| 2017/0105745 A1 | 4/2017 | Rosenbluth et al. |
| 2017/0172603 A1 | 6/2017 | Bonnette et al. |
| 2017/0181760 A1 | 6/2017 | Look et al. |
| 2017/0216503 A1 | 8/2017 | Look et al. |
| 2017/0245885 A1 | 8/2017 | Lenker |
| 2017/0265885 A1 | 9/2017 | Bonnette et al. |
| 2017/0281204 A1 | 10/2017 | Garrison et al. |
| 2017/0290598 A1* | 10/2017 | Culbert ............ A61M 25/0026 |
| 2018/0207397 A1* | 7/2018 | Look ................ A61M 25/0068 |
| 2018/0214172 A1 | 8/2018 | Donnelly et al. |
| 2018/0338770 A1 | 11/2018 | Mogi et al. |
| 2018/0368876 A1 | 12/2018 | Malhi et al. |
| 2019/0328412 A1 | 10/2019 | Mazhar et al. |
| 2019/0381223 A1* | 12/2019 | Culbert ................ A61M 1/85 |
| 2020/0022711 A1* | 1/2020 | Look ..................... A61M 1/815 |
| 2020/0345904 A1* | 11/2020 | Casey ............... A61M 25/0097 |
| 2020/0367917 A1 | 11/2020 | Teigen et al. |

FOREIGN PATENT DOCUMENTS

| | | |
|---|---|---|
| CN | 201603160 U | 10/2010 |
| CN | 103767760 A | 5/2014 |
| DE | 3715418 A1 | 11/1987 |
| DE | 4018736 A1 | 1/1992 |
| EP | 0709110 A1 | 5/1996 |
| EP | 0726466 A1 | 8/1996 |
| EP | 0806213 A1 | 11/1997 |
| EP | 1092396 A2 | 4/2001 |
| EP | 1488748 A1 | 12/2004 |
| EP | 2301450 A1 | 3/2011 |
| EP | 2859902 A1 | 4/2015 |
| EP | 2131759 B1 | 10/2017 |
| JP | 06-125915 A | 5/1994 |
| JP | 06-205784 A | 7/1994 |
| JP | 06-205785 A | 7/1994 |
| JP | 07-299078 A | 11/1995 |
| JP | 2001-161700 A | 6/2001 |
| JP | 2003-010194 A | 1/2003 |
| JP | 2003-101194 A | 4/2003 |
| JP | 2003-514632 A | 4/2003 |
| JP | 2003-260127 A | 9/2003 |
| JP | 2003-290236 A | 10/2003 |
| JP | 2004-514466 A | 5/2004 |
| JP | 2007-160109 A | 6/2007 |
| JP | 2009-039216 A | 2/2009 |
| JP | 2013-154171 A | 8/2013 |
| JP | 2013-180156 A | 9/2013 |
| WO | 90/05493 A1 | 5/1990 |
| WO | 96/01079 A1 | 1/1996 |
| WO | 96/35469 A1 | 11/1996 |
| WO | 99/01079 A1 | 1/1999 |

(56) References Cited

FOREIGN PATENT DOCUMENTS

| | | |
|---|---|---|
| WO | 99/18850 A1 | 4/1999 |
| WO | 00/69348 A1 | 11/2000 |
| WO | 01/37916 A1 | 5/2001 |
| WO | 02/19928 A2 | 3/2002 |
| WO | 02/26289 A1 | 4/2002 |
| WO | 2004/100772 A2 | 11/2004 |
| WO | 2005/004968 A1 | 1/2005 |
| WO | 2006/081238 A2 | 8/2006 |
| WO | 2007/087404 A2 | 8/2007 |
| WO | 2007/143633 A2 | 12/2007 |
| WO | 2008/097993 A2 | 8/2008 |
| WO | 2008/121481 A1 | 10/2008 |
| WO | 2010/023617 A1 | 3/2010 |
| WO | 2010/023671 A2 | 3/2010 |
| WO | 2015/179329 A1 | 11/2015 |
| WO | 2016/126974 A1 | 8/2016 |
| WO | 2017/112922 A1 | 6/2017 |
| WO | 2018/215840 A1 | 11/2018 |

OTHER PUBLICATIONS

Comparison of Dimensions and Aspiration Rate of the Pronto V3, Pronto LP, Export XT, Export AP, Fetch, Xtract, Diver C.E, and QuickCat Catheter, Vascular Solutions, Inc., downloaded from internet Oct. 22, 2014.
Dalal, J., Sahoo, P., Dhall, A., Kapoor, R., Krishnamurthy, A., Shetty, S., Trivedi, S., Kahali, D., Shah, B., Chockalingam, K., Abdullakutty, J., Shetty, P., Chopra, A., Ray, R., Desai, D., Pachiyappan, Ratnaparkhi, G., Sharma, M., Sambasivam, K. "Role of thrombysis in reperfusion therapy for management of AMI: Indian scenario," Indian Heart Journal, 2013, pp. 566-585, vol. 63, Cardiological Society of India, Bombay, India.
Franetzki, M., "Confusion in the Terminology of Insulin Devices", Diabetes Care, Jan.-Feb. 1982, pp. 74-75, vol. 5, No. 1, American Diabetes Association, Alexandria, USA.
Frolich, G., Meier, P., White, S., Yellon, D., Hausenloy, D., "Myocardial reperfusion injury: looking beyond primary PCI", European Heart Journal Jun. 2013, pp. 1714-1722, vol. 34, No. 23, Elsevier, Amsterdam, The Netherlands.
Gousios, A, Shearn, M, "Effect of Intravenous Heparin on Human Blood Viscosity", Circulation, Dec. 1959, pp. 1063-1066, vol. 20, American Heart Association, Dallas, USA.
Harvard Health; Normal Body Temperature: Rethinking the normal human body temperature; p. 1; published Apr. 1, 2006; http://www.health.harvard.edu/press.sub.—releases/normal.sub.—body.sub.—temperature.
Infusion Liquid Flow Sensors-Safe, Precise and Reliable, Sensirion, downloaded from Internet Apr. 3, 2015.
Irsigler, K, Kritz, H., Hagmuller, G., Franezki, M., Prestele, K, Thurow, H., Geisen, K., "Long-term Continuous Intraperitoneal Insulin Infusion with an Implanted Remote-Controlled Insulin Infusion Device", Diabetes, Dec. 1981, pp. 1072-1075, vol. 30, No. 12, American Diabetes Association, New York, USA.
Kritz, H., Hagmuller, G, Lovett, R., Irsigler, K., "Implanted Constant Basal Rate Insulin Infusion Devices for Type 1 (Insulin-Dependent) Diabetic Patients", Diabetologia, Aug. 1983, pp. 78-81, vol. 25, No. 2, Springer-Verlag, Berlin, Germany.
Lipinski, M., Lee, R., Gaglia, M., Torguson, R., Garcia-Garcia, H., Pichard, A., Satler, L., Waksman, R. "Comparison of heparin, bivalirudin, and different glycoprotein IIb/IIIa inhibitor regimens for anticoagulation during percutaneous coronary intervention: a network meta-analysis," Cardiovascular Revascularization Medicine, 2016, pp. 535-545, vol. 17, Elsevier, New York, USA.

Makes even the most difficult intervention a Fast and Smooth Run. GuideLiner brochure. Vascular Solutions,. Inc., downloaded from internet Apr. 9, 2015.
Metzler, L., "Miniature Sensor Combines with Micropump to Control Drug Delivery", Medical Design Technology, Mar. 2017, pp. 22-23, MDTmag.com, Advantage Business Media, Rockaway, USA.
Micossi, P., Cristallo, M., Galberti, G, Librenti, M., Petrella, G., Pozza, G., Hutter, R., Babic, D., Hagmuller, G., Veit, F., Irsigler, K., Walter, H., Ladik, T., Flaschentrager, T., Gunther, A., Kronski, K., Mehnert, H., Bauersachs, R., Ruhland, B., Piwernetz, K., Renner, R., Hepp, K., Buchholz, G., Kollert, D., Wohlers, C,, Jahrling, P., Franetzki, M., Pfeiffer, C., Neuhauser, C., Seipke. G., Deutschlander. N., Zoltobrocki, M., "One-Year Trial of a Remote-Controlled Implantable Insulin Infusion System in Type I Diabetic Patients", The Lancet, Oct. 15, 1988, pp. 866-869, vol. 2, No.
Parikh, A., Ali, F., "Novel Use of GuideLiner Catheter to Perform Aspiration Thrombectomy in a Saphenous Vein Graft" Cath Lab Digest, Oct. 2013, downloaded from internet Oct. 22, 2014.
Pechlaner, C., Knapp, E., Wiedermann, C. "Hypersensitivity reactions associated with recombinant tissue-type plasminogen activator and urokinase, " Blood Coagulation and Fibrinolysis, 2001, pp. 491-494, vol. 12, Lippincott Williams & Wilkins, Hagerstown, USA.
Prasad, A., Stone, G., Holmes, D., Gersh, B., Peperfusion Injury, Microvascular Dysfunction, and Carioprotection: The "Dark Side" of Reperfusion, Circulation, Nov. 24, 2009, pp. 2105-2112, vol. 120, American Heart Association, Dallas, USA.
Principles and Practice of Pharmacology for Anaesthetists, ed. Calvey, T., Williams, N., 2008, pp. 324-327, 5th Edition, Blackwell Publishing, Malden, USA.
Puddu, P., Ianetta, L., Placanica, A., Cuturello, D., Schiariti, M., Manfrini, O., "The role of Glycoprotein IIb/IIIa inhibitors in acute coronary syndromes and the interference with anemia," International Journal of Cardiology, 2016, pp. 1091-1096, vol. 222, Elsevier, Amsterdam, The Netherlands.
Rodriquez, R., Conde-Green, A., "Quantification of Negative Pressures Generated by Syringes of Different Calibers Used for Liposuction", Plastic & Reconstructive Surgery, Aug. 2012; pp. 383e-384e, vol. 130, No. 2, Lippicott Williams & Wilkins, Philadelphia, USA.
Saudek, C., Selam, J-L, Pitt, H., Waxman, K., Rubio, M., Jeandidier, N., Turner, D., Fischell, R., Charles, M., "A Preliminary trial of the Programmable Implantable Medication System for Insulin Delivery", The New England Journal of Medicine, Aug. 31, 1989, pp. 574-579, vol. 321, No. 9, Massachusetts Medical Society, Boston, USA.
Selam, J-L, "Development of Implantable Insulin Pumps: Long is the Road", Diabetic Medicine, Nov. 1988, pp. 724-733, vol. 5, No. 8, Wiley, Chichester, UK.
Stys, A., Stys, T., Rajpurohit, N., Khan, M. "A Novel Application of GuideLiner Catheter for Thrombectomy in Acute Myocardial Infarction: a Case Series", Journal of Invasive cardiology, Nov. 2013, pp. 620-624, vol. 25, No. 11, King of Prussia, USA.
Van De Werf, F, "The ideal fibrinolytic: can drug design improve clinical results?" European Heart Journal, 1999, pp. 1452-1458, vol. 20, Elsevier, Amsterdam, The Netherlands.
Warmerdam, P., Vanderlick, K., Vandervoort, P., de Smedt, H., Plaisance, S., De Maeyer, M., Collen, D. "Saphylokinase-Specific-Cell-Mediated Immunity in Humans, " The Journal of Immunology, 2002, pp. 155-161, vol. 168, Williams & Wilkins Co., Baltimore, USA.
Extended European Search Report dated Aug. 31, 2018, in EP App. No. 16843162.5 filed Sep. 3, 2016 (10 pages).
PCT International Search Report and Written Opinion for PCT/US2016/050302, Applicant: Vesatek, LLC, Forms PCT/ISA/220, 210, and 237 dated Nov. 29, 2016 (10 pages).

\* cited by examiner

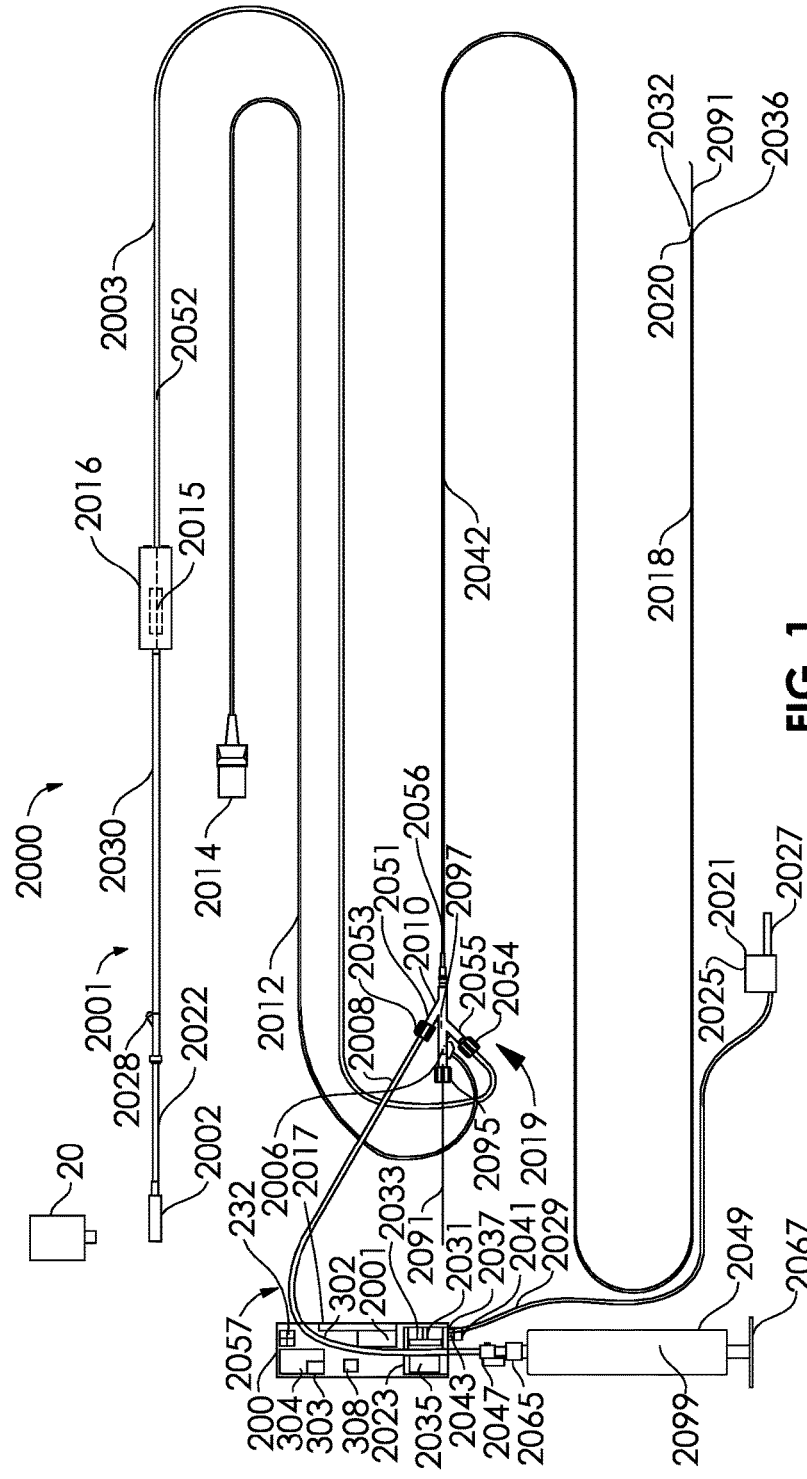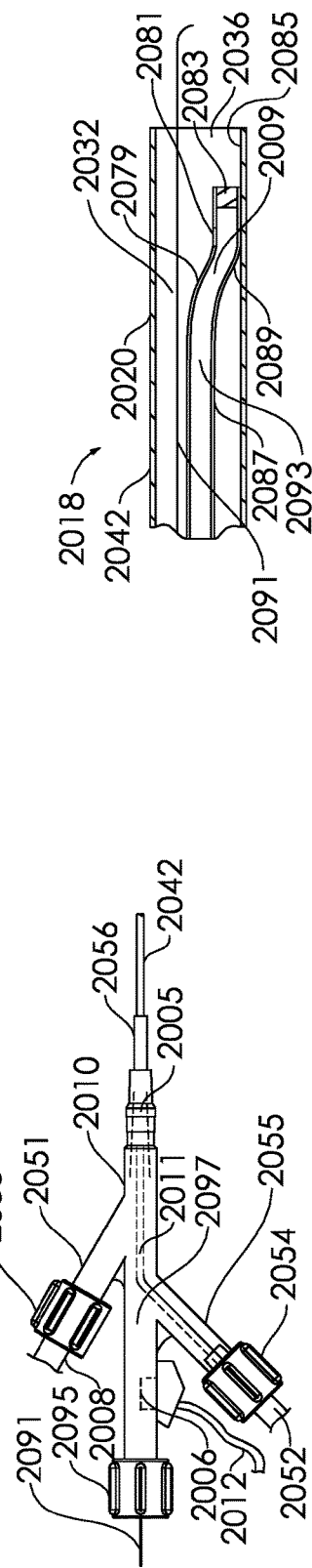

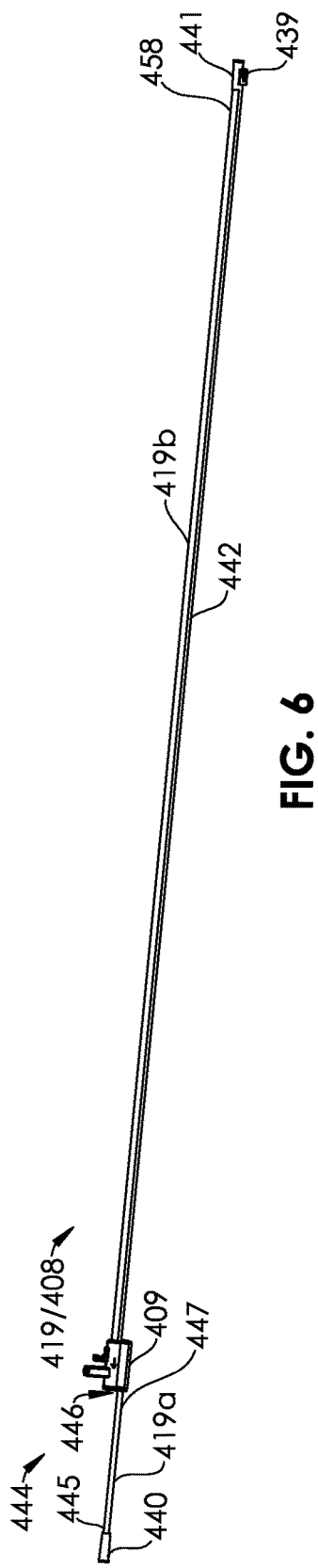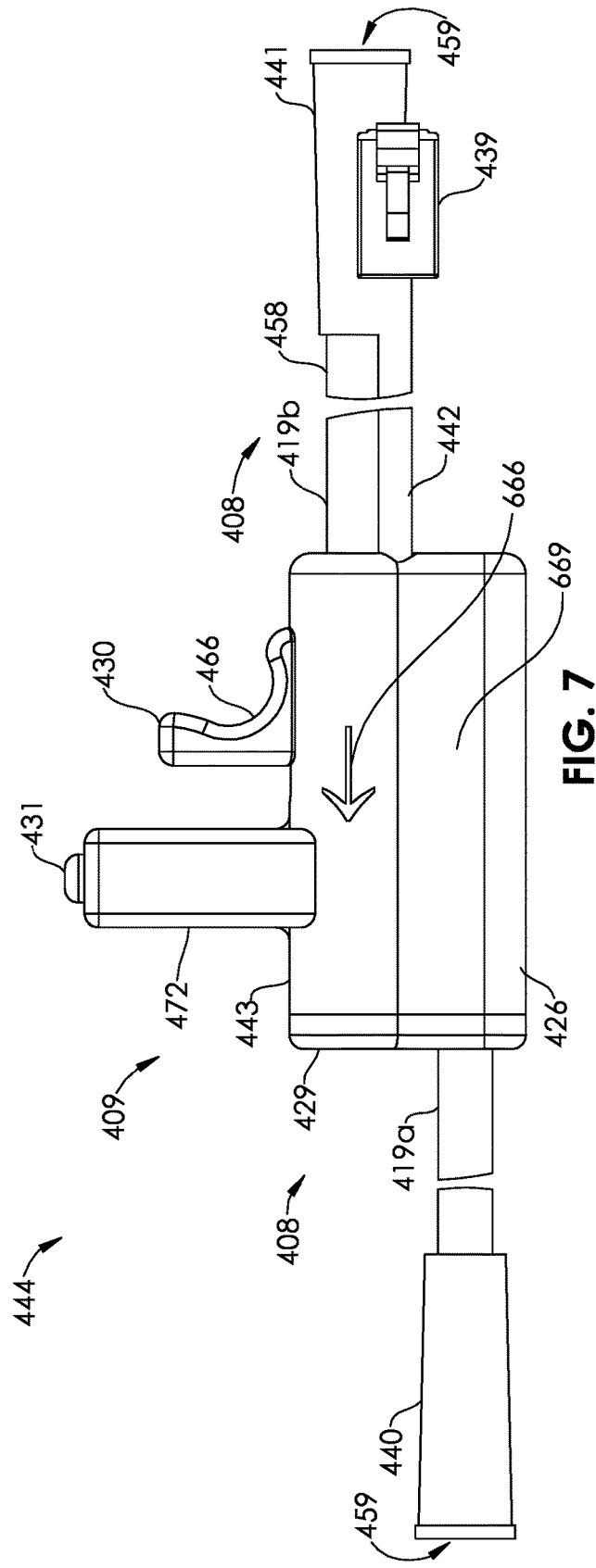

SYSTEMS AND METHODS FOR REMOVAL OF BLOOD AND THROMBOTIC MATERIAL

This application is a continuation of U.S. patent application Ser. No. 17/671,462, filed Feb. 14, 2022, which claims the benefit of and priority to U.S. Provisional Patent Application No. 63/149,623, filed on Feb. 15, 2021, which are incorporated by reference herein in their entireties for all purposes. Priority is claimed pursuant to 35 U.S.C. § 119 and 35 U.S.C. § 120.

BACKGROUND OF THE INVENTION

Field of the Invention

The present disclosure pertains generally to medical devices and methods of their use. More particularly, the present invention pertains to aspiration and thrombectomy devices and methods of use thereof.

Description of the Related Art

Several devices and systems already exist to aid in the removal of thrombotic material. These include simple aspiration tube type devices using vacuum syringes to extract thrombus into the syringe, simple flush-and-aspirate devices, more complex devices with rotating components the pull in, macerate and transport thrombotic material away from the distal tip using a mechanical auger, systems that use very high pressure to macerate the thrombus and create a venturi effect to flush the macerated material away.

All of the devices described above have limitations as a result of individual design characteristics. For example, simple aspiration catheters offer ease of use and rapid deployment but may become blocked or otherwise inoperable when faced with older, more organized thrombotic material. Such devices must be removed and cleared outside the body and then re-inserted into the vasculature, which lengthens the time needed for the procedure and increases the opportunity to kink the catheter shaft. Such kinks may reduce performance by decreasing the cross-sectional area of the catheter or may render the device inoperable.

Mechanical rotary devices use an auger to grab and carry the thrombus away from the target area. Some create transport force via vacuum bottles while others create differential pressure at the distal tip of the device with the auger acting as a low pressure pump. These devices typically work slowly and offer the physician no feedback as to when the device should be advanced further into the lesion.

Flushing type devices include manual flush type devices in which the physician manipulates a hand-driven pump to provide flowing saline at the tip of the device to break up and aspirate the thrombus material, which may introduce performance variations based on the ability of the physician to consistently pump the device over the duration of the procedure. Flushing devices also include high pressure flushing devices that macerate the thrombus and then, using a vortex created by the high pressure fluid, transport the emulsified thrombotic material to a collection bag. These devices are effective at removing all levels of thrombotic material, but the pressure created by the device is so great that its action against certain vessel walls may interrupt the heart muscle stimulation mechanism and create a bradycardia event in certain patients, sometimes requiring that a pacing lead be placed in the patient prior to use. Further, interacting with the thrombotic material outside of the catheter may allow loose material to escape the capture mechanism.

SUMMARY OF THE INVENTION

In one embodiment of the present disclosure, a system for aspirating thrombus includes an aspiration catheter including an elongate shaft configured for placement within a blood vessel of a subject, a supply lumen and an aspiration lumen each extending along a shaft, the supply lumen having a proximal end and a distal end, and the aspiration lumen having a proximal end and a distal opening, and an opening at or near the distal end of the supply lumen, the opening configured to allow injection of pressurized fluid into the aspiration lumen at or near the distal end of the aspiration lumen when the pressurized fluid is pumped through the supply lumen, an extension conduit including a distal end configured to couple to the aspiration lumen of the aspiration catheter, a proximal end configured to couple to a negative pressure source, and a passageway extending between the distal end and the proximal end of the extension conduit, a combined hydraulic and electrical control carried on the extension conduit and including a first control interface and a control body, the first control interface configured to be activated by a user to move the control body between a first position and a second position, an electrical switch configured to be activated by the control body when the control body is moved to the second position, and a valve having a closed position blocking flow through the passageway of the extension conduit and an open position allowing flow through the passageway of the extension conduit, the valve configured to be moved from the closed position to the open position by the control body when the control body is moved to the second position.

In another embodiment of the present disclosure, an extension conduit for use with a system for aspirating thrombus includes a passageway extending between a distal end and a proximal end of the extension conduit, and a combined hydraulic and electrical control carried on the extension conduit and configured to be activated by a user to activate an electric switch while opening a valve to allow flow through the passageway.

In yet another embodiment of the present disclosure, an extension conduit for use with a system for aspirating thrombus includes a passageway extending between a distal end and a proximal end of the extension conduit, and a combined hydraulic and electrical control carried on the extension conduit and configured to be activated by a user to deactivate an electric switch while closing a valve to stop flow through the passageway.

BRIEF DESCRIPTION OF THE DRAWINGS

FIG. 1 is a plan view of disposable components of a system for aspirating thrombus according to an embodiment of the present disclosure.

FIG. 2 is a sectional view of a distal end of the aspiration catheter of the system for aspirating thrombus of FIG. 1.

FIG. 3 is a detail view of a y-connector of the aspiration catheter of the system for aspirating thrombus of FIG. 1.

FIG. 6 is a perspective view of an aspiration tubing set with a control, according to an embodiment of the present disclosure.

FIG. 7 is a plan view of the aspiration tubing sent and control of FIG. 6.

DETAILED DESCRIPTION OF THE ILLUSTRATED EMBODIMENTS

Figure 4:
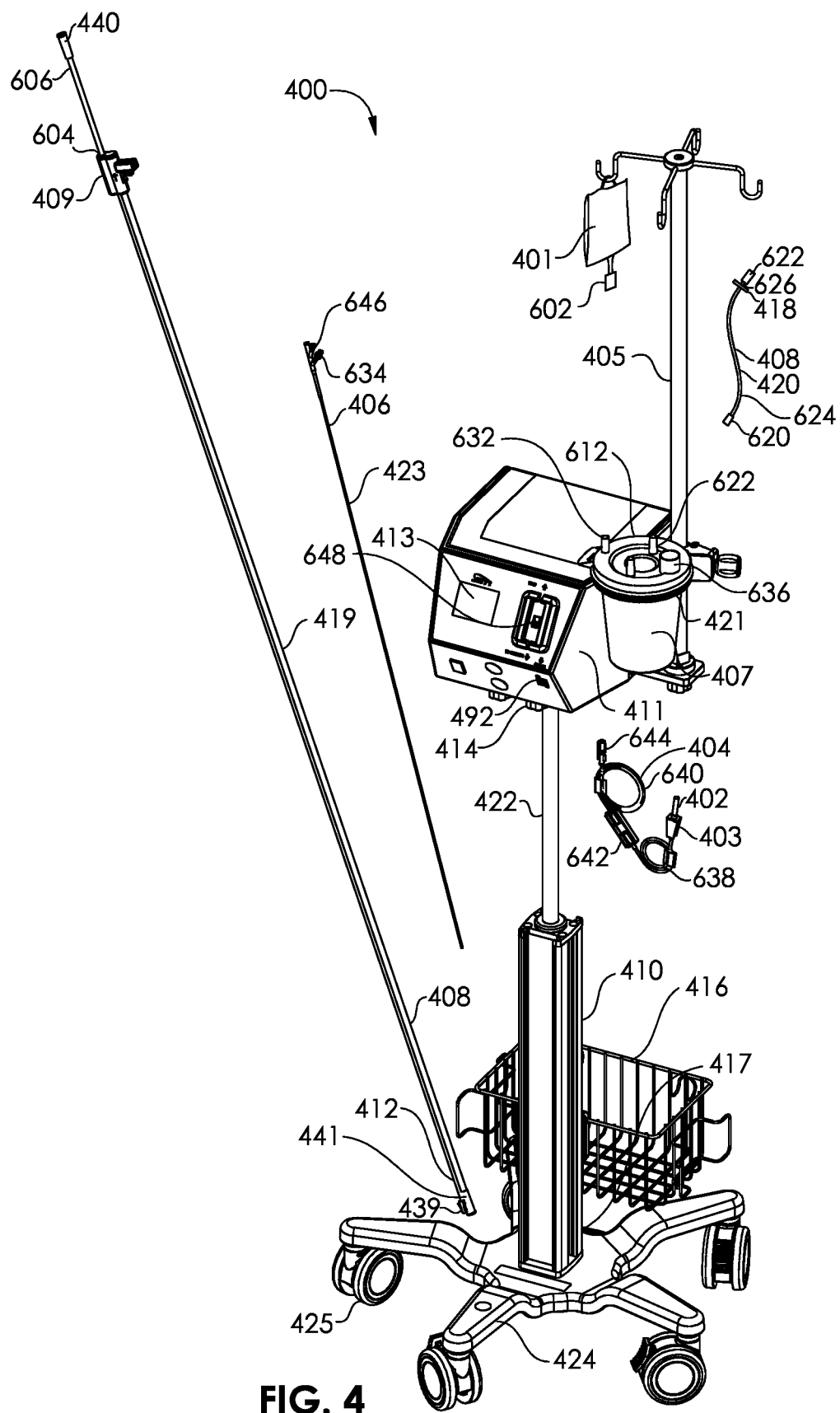
FIG. 4 is a plan view of disposable components of a system for aspirating thrombus according to an embodiment of the present disclosure.

A system for aspirating thrombus 2000 is illustrated in FIG. 1. The system for aspirating thrombus 2000 includes three major components: a pump 200, an aspiration catheter 2018, and a tubing set 2003. The aspiration catheter 2018 and the tubing set 2003 represent disposable components 2001, and the pump 200, and the pump's associated pump base, is a reusable component. It is not necessary to sterilize the pump 200 as it may be kept in a non-sterile field or area during use. The aspiration catheter 2018 and the tubing set 2003 may each be supplied sterile, after sterilization by ethylene oxide gas, electron beam, gamma, or other sterilization methods. The aspiration catheter 2018 may be packaged and supplied separately from the tubing set 2003, or the aspiration catheter 2018 and the tubing set 2003 may be packaged together and supplied together. Alternatively, the aspiration catheter 2018 and tubing set 2003 may be packaged separately, but supplied together (i.e., bundled). The aspiration catheter 2018 has a distal end 2020 and includes an over-the-wire guidewire lumen/aspiration lumen 2032 extending between an open distal end 2036, and a proximal end 2019 comprising a y-connector 2010. The catheter shaft 2042 of the aspiration catheter 2018 is connected to the y-connector 2010 via a protective strain relief 2056. In other embodiments, the catheter shaft 2042 may be attached to the y-connector 2010 with a luer fitting. The y-connector 2010 comprises a first female luer 2055 which communicates with a catheter supply lumen 2093 (FIG. 2), and a second female luer 2051 which communicates with the guidewire lumen/aspiration lumen 2032.

A spike 2002 for coupling to a fluid source 20 (e.g., saline bag, saline bottle) allows fluid to enter through an extension tubing 2022 and flow into a supply tube 2030. An optional injection port 2028 allows injection of materials or removal of air, as described in relation to previous embodiments. A cassette 2016 having a moveable piston 2015 is used in conjunction with a mechanical actuator 2017 of the pump 200. Fluid is pumped into an injection tube 2052 from action of the cassette 2016 as applied by the actuator 2017 of the pump 200. A male luer 2054, hydraulically communicating with the catheter supply lumen 2093, via the injection tube 2052, is configured to attach to the female luer 2055 of the y-connector 2010.

Accessories 2057 are illustrated that are intended for applying a vacuum source, such as a syringe 2049 having a plunger 2067 and a barrel 2099, to the aspiration lumen 2032 of the catheter 2018. The syringe 2049 is attached to a vacuum line 2008 via the luer 2065 of the syringe 2049. A stopcock 2047 may be used on the luer 2065 to maintain the vacuum, or alternatively, the plunger 2067 may be a locking variety of plunger that is configured to be locked in the retracted (vacuum) position. A male luer 2053 at the end of the vacuum line 2008 may be detachably secured to the female luer 2051 of the y-connector 2010 of the aspiration catheter 2018. As shown in more detail in FIG. 3, a pressure sensor or transducer 2006 is secured inside an internal cavity 2097 of the y-connector 2010 proximal to the female luer 2055 and the female luer 2051. A valve 2095, for example a Touhy-Borst, at the proximal end of the y-connector 2010 allows hemostasis of the guidewire lumen/aspiration lumen 2032 around a guidewire 2091. In other embodiments, the valve 2095 may comprise a longitudinally spring-loaded seal. The guidewire 2091 may be inserted entirely through the guidewire lumen/aspiration lumen 2032. Signals output from the pressure sensor 2006 are carried through a cable 2012 to a connector 2014. The connector 2014 is plugged into a socket 308 of the pump 200. Pressure related signals may be processed by a circuit board 304 of the pump 200. The pressure transducer 2006 may be powered from the pump 200, via the cable 2012. The accessories 2057 may also be supplied sterile to the user.

A foot pedal 2021 is configured to operate a pinch valve 2023 for occluding or opening the vacuum line 2008. The foot pedal 2021 comprises a base 2025 and a pedal 2027 and is configured to be placed in a non-sterile area, such as on the floor, under the procedure table/bed. The user steps on the pedal 2027 causing a signal to be sent along a cable 2029 which is connected via a plug 2041 to an input jack 2037 in the pump 200. The vacuum line 2008 extends through a portion of the pump 200. The circuit board 304 of the pump may include a controller 303 configured to receive one or more signals indicating on or off from the foot pedal 2021. The controller of the circuit board 304 may be configured to cause an actuator 2031 carried by the pump 200 to move longitudinally to compress and occlude the vacuum line 2008 between an actuator head 2033 attached to the actuator 2031 and an anvil 2035, also carried by the pump 200. By stepping on the pedal 2027, the user is able to thus occlude the vacuum line 2008, stopping the application of a negative pressure. Also, by stepping on the pedal 2027, the user may cause the opposite action, wherein the actuator head 2033 opens the vacuum line 2008, by moving away from the anvil 2035. The anvil 2035 may have a flat (planar) shape, or a U-shape (e.g., semi-cylindrical), or a V-shape (e.g., a V-block) where it contacts the tubing of the vacuum line 2008. Furthermore, the actuator head 2033 may have a flat (planar) shape, or a U-shape (e.g., semi-cylindrical), or a V-shape (e.g., a V-block) where it contacts the vacuum line 2008. The foot pedal 2021 may operate by alternately causing the actuator 2031 to move in a first direction and a second, opposite direction, respectively, with alternate hits on the pedal 2027. In some embodiments, as the pedal 2027 of the foot pedal 2021 is depressed, the controller may be configured to open the pinch valve 2023.

The pressure transducer 2006 thus senses a negative pressure and sends a signal, causing the controller to start the motor 302 of the pump 200. As the effect via the electronics is substantially immediate, the motor 302 starts pumping almost immediately after the pedal 2027 is depressed. As the pedal 2027 of the foot pedal 2021 is released, the controller then causes the pinch valve 2023 to close. The pressure transducer 2006 thus senses that no negative pressure is present and the controller 303 causes the motor 302 of the pump 200 to shut off. Again, the effect via the electronics is substantially immediate, and thus the motor 302 stops pumping almost immediately after the pedal 2027 is depressed. During sterile procedures, the main interventionalist is usually "scrubbed" such that the hands only touch items in the sterile field. However, the feet/shoes/shoe covers are not in the sterile field. Thus again, a single user may operate a switch (via the pedal 2027) while also manipulating the catheter 2018 and guidewire 2091. However, this time, it is the sterile field hands and non-sterile field feet that are used. Alternatively, the foot pedal 2021 may comprise two pedals, one for occlude and one for open. In an alternative foot pedal embodiment, the pedal 2027 may operate a pneumatic line to cause a pressure activated valve or a cuff to occlude and open the vacuum line 2008, for example, by forcing the actuator head 2033 to move. In another alternative embodiment, the pedal 2027 may turn, slide, or otherwise move a mechanical element, such as a flexible pull cable or push rod that is coupled to the actuator 2031, to move the actuator head 2033. The cable 2029 may be supplied sterile and connected to the base 2025 prior to a procedure. The occlusion and opening of the vacuum line 2008 thus acts as an on and off switch for the pump 200 (via the pressure sensor 2006). The on/off function may thus be performed by a user whose hands can focus on manipulating sterile catheters, guidewires, and accessories, and whose foot can turn the pump on and off in a non-sterile environment. This allows a single user to control the entire operation or the majority of operation of the system for aspirating thrombus 2000. This can be an advantage both in terms of a rapid, synchronized procedure, but is also helpful in laboratories where additional assistants are not available. The actuator 2031 and anvil 2035 may be controlled to compress the vacuum line 2008 with a particular force, and the actuator 2031 may be controlled to move at a particular speed, either when compressing or when removing compression. Speed and force control allows appropriate response time, but may also be able to add durability to the vacuum line 2008, for example, by not overcompressing.

The foot pedal 2021 may communicate with the pinch valve 2023 via a wired connection through the pump 200 or may communicate with the pinch valve 2023 wirelessly.

Returning to FIG. 1, the plug 2041 contains an identification component 2043, which may be read by the circuitry (e.g., circuit board 304) coupled to the input jack 2037 of the pump 200. In some embodiments, the identification component 2043 comprises a resistor having a particular value. When the plug 2041 is connected to the input jack 2037, the circuitry of the input jack 2037 sends a current through the resistor, resulting in the pump 200 being electronically placed into a "foot pedal" mode, wherein the foot pedal 2021 can be used to control the operation of the pinch valve 2023. Alternatively, when the plug 2041 is detached from the input jack 2037, and the circuitry is not able to identify the resistor, the pump 200 is placed in a "manual" mode, wherein the pump is controllable only by buttons 232. In other embodiments, instead of a resistor, the identification component 2043 may comprise an RFID (radio-frequency identification) chip, which is read by the circuitry when the plug 2041 is connected to the input jack 2037. In other embodiments, a proximity sensor, such as a Hall-effect device, may be utilized to determine whether the plug 2041 is or is not connected to the input jack 2037.

In should be noted that in certain embodiments, the pinch valve 2023 and the foot pedal 2021 may be incorporated for on/off operation of the pinch valve 2023 on the vacuum line 2008, without utilizing the pressure sensor 2006. In fact, in some embodiments, the pressure sensor 2006 may even be absent from the system for aspirating thrombus 2000, the foot pedal 2021 being used as a predominant control means.

Turning to FIG. 2, a supply tube 2087, which contains the catheter supply lumen 2093, freely and coaxially extends within the over-the-wire guidewire lumen/aspiration lumen 2032. At least a distal end 2089 of the supply tube 2087 is secured to an interior wall 2085 of the guidewire lumen/aspiration lumen 2032 of the catheter shaft 2042 by adhesive, epoxy, hot melt, thermal bonding, or other securement modalities. A plug 2083 is secured within the catheter supply lumen 2093 at the distal end 2089 of the supply tube 2087. The plug 2083 blocks the exit of pressurized fluid, and thus the pressurized fluid is forced to exit through an orifice 2081 in the wall 2079 of the supply tube 2087. The orifice 2081 may comprise a number of different shapes, including but not limited to a circular hole, an oval hole, an elliptical hole, a longitudinally-extending slit, a circumferentially-extending slit, or combinations and modifications thereof. The free, coaxial relationship between the supply tube 2087 and the catheter shaft 2042 along their respective lengths, allows for improved flexibility. In some embodiments, in which a stiffer proximal end of the aspiration catheter 2018 is desired (e.g., for pushability or even torquability), the supply tube 2087 may be secured to the interior wall 2085 of the guidewire lumen/aspiration lumen 2032 of the catheter shaft 2042 along a proximal portion of the aspiration catheter 2018, but not along a distal portion. This may be appropriate if, for example, the proximal portion of the aspiration catheter 2018 is not required to track through tortuous vasculature, but the distal portion is required to track through tortuous vasculature. The free, substantially unconnected, coaxial relationship between the supply tube 2087 and the catheter shaft 2042 along their respective lengths, may also be utilized to optimize flow through the guidewire lumen/aspiration lumen 2032, as the supply tube 2087 is capable of moving out of the way due to the forces of flow (e.g., of thrombus/saline) over its external surface, such that the remaining inner luminal space of the guidewire lumen/aspiration lumen 2032 self-optimizes, moving toward the lowest energy condition (least fluid resistance) or toward the largest cross-sectional space condition (e.g., for accommodating and passing pieces of thrombus).

Figure 5:
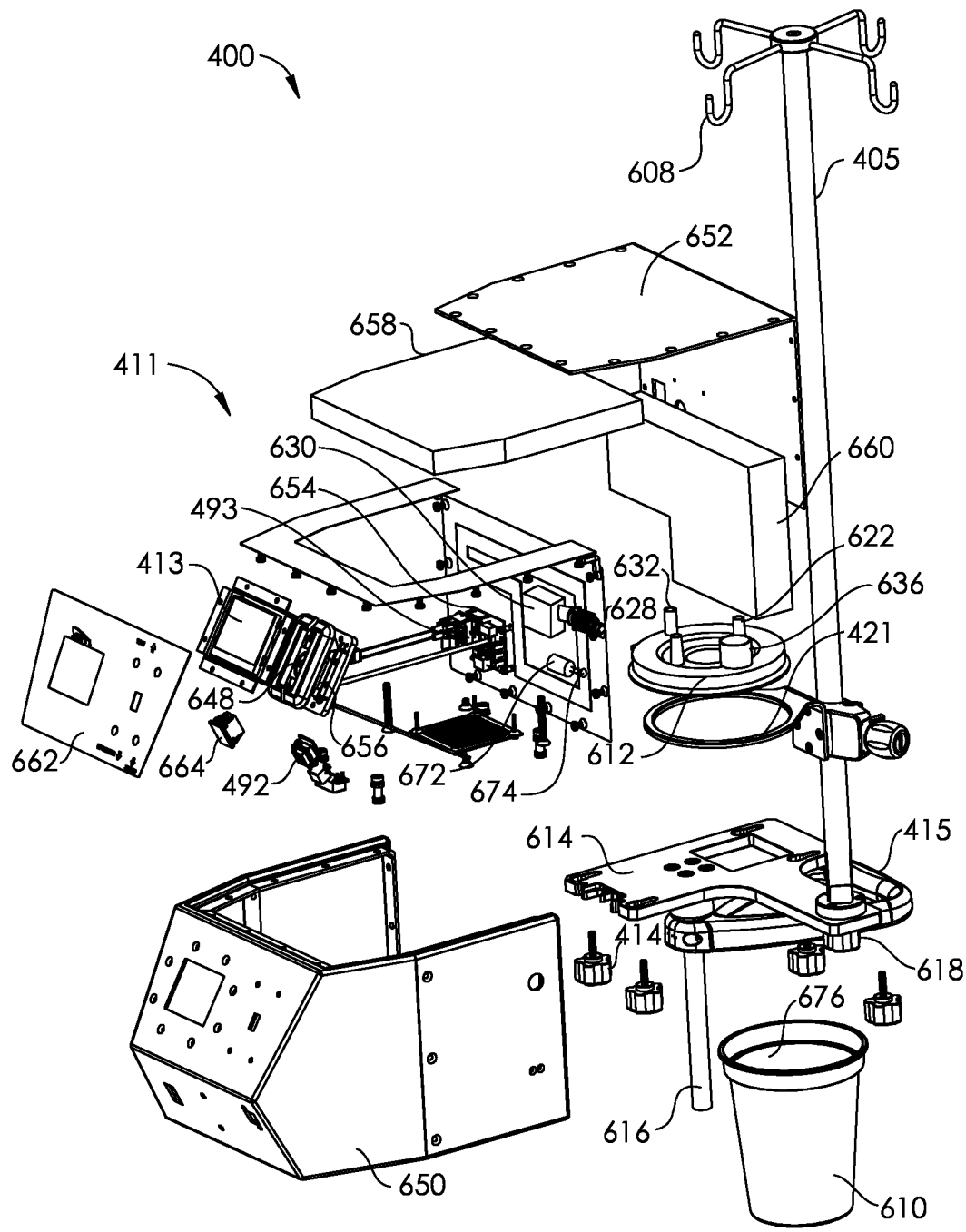
FIG. 5 is a perspective view of the system for aspirating thrombus of FIG. 4.

A system for aspirating thrombus 400 is illustrated in FIGS. 4-5. An aspiration catheter 406 is similar to the aspiration catheter 2018 of FIGS. 1-3. The aspiration catheter 406 is configured for aspirating thrombus from peripheral vessels, but may also be configured with a size for treating coronary, cerebral, pulmonary or other arteries, or veins. The aspiration catheter 406/system 400 may be used in interventional procedures, but may also be used in surgical procedures. The aspiration catheter 406/system 400 may be used in vascular procedures, or non-vascular procedures (other body lumens, ducts, or cavities). The catheter 406 comprises an elongate shaft 423 configured for placement within a blood vessel of a subject; a catheter supply lumen 2093 (FIG. 2) and a guidewire/aspiration lumen 2032, each extending along the shaft, the supply lumen 2093 having a proximal end 2011 and a distal end 2009, and the aspiration lumen 2032 having a proximal end 2005 (FIG. 3) and an open distal end 2036 (FIG. 2); and an orifice or opening 2081 at or near the distal end 2009 of the supply lumen 2093, the opening configured to allow the injection of pressurized fluid into the aspiration lumen 2032 at or near the distal end 2036 of the aspiration lumen 2032 when the pressurized fluid is pumped through the supply lumen 2093. In some embodiments, the orifice or opening 2081 may be located proximal to the distal end 2009 of the supply lumen 2093. In some embodiments, the distal end 2009 of the supply lumen 2093 may comprise a plug 2083. A pump set 404 (e.g., tubing set) is configured to hydraulically couple the supply lumen 2093 to a pump within a saline drive unit (SDU) 411, for injecting pressurized fluid (e.g., saline, heparinized saline) through the supply lumen 2093. Suction tubing 408, comprising sterile suction tubing 419 and non-sterile suction tubing 420, is configured to hydraulically couple a vacuum canister 407 to the aspiration lumen 2032. A filter 418 may be carried in-line on the suction tubing 408, for example, connected between the sterile suction tubing 419 and the non-sterile suction tubing 420, or on the non-sterile suction tubing 420. The filter 418 is configured to capture large elements such as large pieces of thrombus or emboli.

The pump set 404 includes a saline spike 402 for connection to a port 602 of a saline bag 401, and an inline drip chamber 403 for visually assessing the movement of saline, as well as keeping air out of the fluid being injected. The saline bag 401 may be hung on an IV pole 405 on one or more hooks 608. A pressure sensor 604 such as a vacuum sensor may be used within any lumen of the pump set 404, the suction tubing 408, the supply lumen 2093 or aspiration lumen 2032 of the catheter 406, or any other component which may see fluid flow. The pressure sensor 604 is shown in FIG. 4 within a lumen at a junction between a first aspiration tube 606 and a control 409. A cable 412 carries signals output from the pressure sensor 604 to a controller 493 in the SDU 411. A connector 439, electrically connected to the cable 412, is configured to be detachably coupled to a mating receptacle 492 (e.g., input jack) in the SDU 411. The SDU 411 also may have a display 413, including an LCD screen or alternative screen or monitor, in order to visually monitor parameters and status of a procedure. In alternative embodiments, the pressure sensor 604 may be replaced by another type of sensor that is configured to characterize fluid flow. In some embodiments, the sensor is a flow sensor, such as a Doppler flow velocity sensor.

Aspirant (e.g., clot, thrombus, blood) that is evacuated from the patient through the aspiration lumen 2032 is collected in the vacuum canister 407. The canister is held in a canister mount 421 carried by the IV pole 405, or alternatively carried by any other part of the system 400. The vacuum canister 407 comprises a receptacle 610 and a lid 612 configured to snappingly cover a portion of the receptacle 610 to close the interior 676 of the receptacle 610. Alternatively, the lid 612 may couple to the receptacle 610 by screwing, clipping, friction fitting, or other manners. The SDU 411 is held on a mount 614 by four locking knobs 414. The mount 614 is secured to a telescoping rod 422 that is adjustable from a cart base 410 via a cart height adjustment knob or other element 417. The mount 614 and a handle 415 are secured to the rod 422 via an inner post 616 that is insertable and securable within an inner cavity in the rod 422. The IV pole 405 secures to the mount 614 via a connector 618. The base 410 includes legs 424 having wheels 425 (e.g., three or more wheels or four or more wheels) and is movable via the handle 415, for instance. The system 400 may also carry a basket 416 for placement of components, products, documentation, or other items.

In use, a user connects a first connector 620 at a first end 624 of the suction tubing 420 to a port 622 on the lid 612 of the canister 407, and connects a second connector 441 at a second end 626 of the suction tubing 420 to a vacuum pump input 628 in the SDU 411. A vacuum pump 630 may be carried within the SDU 411 in order to maintain a vacuum/negative pressure within the canister 407. Alternatively, the vacuum inside the canister 407 may be maintained manually, without a vacuum pump, by evacuating the canister 407 via one or more additional ports 632. A user connects a first connector 440 of the sterile suction tubing 419 to an aspiration luer 634 of the aspiration catheter 406 (similar to luer 2051), and connects a second connector 441 of the sterile suction tubing 419 to port 636 in the lid 612 of the canister 407. Connector 439 is then coupled to the mating receptacle in the SDU 411 for communication with the control 409 and/or the pressure sensor 604. For instance, the connector 439 can be snapped into mating receptacle 492 in the SDU 411 for communication with elements of the control 409 and/or for communication with the pressure sensor 604, either via cable 412, and/or additional cables or wires. The control 409 is configured for controlling the operation of the system and will be described in more detail herein. Alternatively, the connector 439 may couple to the mating receptacle 492 by clipping, friction fitting, vacuum fitting, or other manners.

After allowing saline to purge through the supply tube 638, cassette 642, and injection tube 640 of the pump set 404, the user connects the luer connector 644 of the pump set 404 to a luer 646 of the aspiration catheter 406 (similar to luer 2055). The cassette 642 (similar to cassette 2016) is then attached to a saddle 648 in the SDU 411. The saddle 648 is configured to reciprocate a piston to inject the saline from the IV bag 401 at high pressure, after the cassette 2016 is snapped in place, keeping the internal contents (e.g., saline) sterile. Systems configured for performing this type of sterile injection of high pressure saline are described in U.S. Pat. No. 9,883,877, issued Feb. 6, 2018, and entitled, "Systems and Methods for Removal of Blood and Thrombotic Material", which is incorporated by reference in their entirety for all purposes. The SDU 411 is enclosed within a case 650 and a case lid 652. The controller 493 may reside on a circuit board 654. Noise from a motor 656 controlling the saddle 648 and from the vacuum pump 630 is abated by internal foam sections 658, 660. The saddle 648 may be moved directly by the motor 656, or may be moved with pneumatics, using a cycled pressurization. An interface panel 662 provides one or more switch 664 and the display 413. Alternatively, the cassette 2016 may couple to the saddle 648 by clipping, friction fitting, vacuum fitting, or other manners.

FIGS. 6-12 illustrate an aspiration tubing set 444 comprising sterile suction tubing 419 and the control 409. A housing 443 comprises a first housing half 426 and a second housing half 427, each configured to house several components, and to close on one another, and to attach to one another. The halves 426, 427 may be bonded together with adhesive, epoxy, or fused with ultrasonic welding or solvent welding, or may be secured together with screws or other connecting elements. As shown in FIG. 6, an aspiration passage from the aspiration lumen 2032 of the aspiration catheter 406 extends from left to right. A first connector 440 may be a luer fitting configured to sealingly attach to the luer 2051. However, alternatively, the luer 2051 may be replaced by a barb and the first connector 440 may be a suction connector, for example a 22 French silicone suction connector. The first connector 440 is sealingly secured to a first end 445 of a first sterile suction tubing 419a, which extends into an inlet 446 of the control 409 at its second end 447. The inlet 446 comprises a hole within an end cover 429 that attaches to an end of the halves 426, 427. The second end 447 is frictionally slid over a barb 599 of an elbow fitting 434, which includes an inner passage 448 having a 90° curve 449. In some embodiments, the curve 449 may comprise an acute angle, such as an angle between about 10° and about 80°, or between about 20° and about 70°, or between about 30° and about 60°. The inner passage 448 of the elbow fitting 434 has an inlet 450 and an outlet 451 (see FIG. 10). Surrounding the outlet 451 is a concave radiused surface 452 configured to be sealingly bonded to a convex cylindrical surface 453 on a custom syringe barrel (piston cylinder) 437. An entry orifice 454 passes through a wall 478 of the cylinder 437, starting at the surface 453. In some embodiments, the elbow fitting 434 and the cylinder 437 may be monolithic. For example, they may comprise a single injection-molded or 3D-printed component (or using other additive fabrication methods). A first end 457 of a second sterile suction tubing 419b is frictionally fit over an outer cylindrical surface 455 on a hub 456 of the cylinder 437. In some embodiments, an adhesive, epoxy, or welding may be used to seal the internal wall surface of the tubing 419b to the outer cylindrical surface 455, though the friction fit is sufficient for resisting −1 atmosphere of vacuum. In an alternative embodiment, the hub 456 includes a barb. In a further alternative embodiment, shown in FIGS. 11-12, the first end 457 may be flared and bonded and/or wedged between the halves 426, 427.

Figure 12:
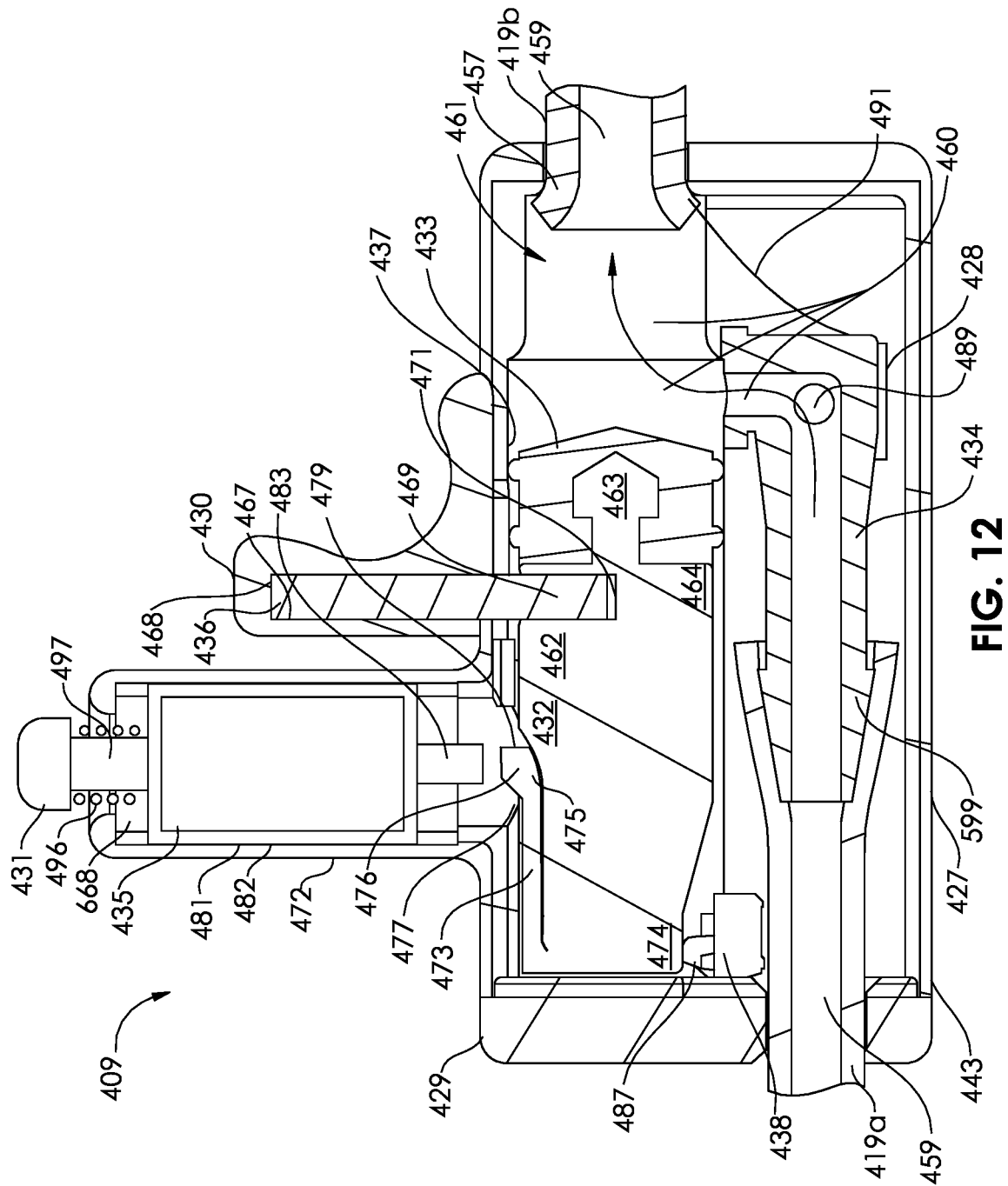
FIG. 12 is a sectional view of the control in an open position, according to an embodiment of the present disclosure.

At a second end 458 of the tubing 419b, a second connector 441 is sealingly bonded. The second connector 441 may be a suction connector, for example a 30 French silicone suction connector. The second connector 441 may be configured to sealingly connect to a port of the cannister 407, or to an intermediate tube that is then attached to the canister 407, or to the filter 418. Thus, from the first connector 440 to the second connector 441, a continuous, contained aspiration passageway 459 is formed. As shown in FIG. 12 by an S-shaped arrow, the passageway 459 comprises an S-duct 460 that is formed by the combination of the suction tubing 419a, the elbow fitting 434, the cylinder 437, and the suction tubing 419b. The passageway 459 is configured for the transport of thrombus and blood from the aspiration lumen 2032 of the aspiration catheter 406 to the canister 407.

Figure 10:
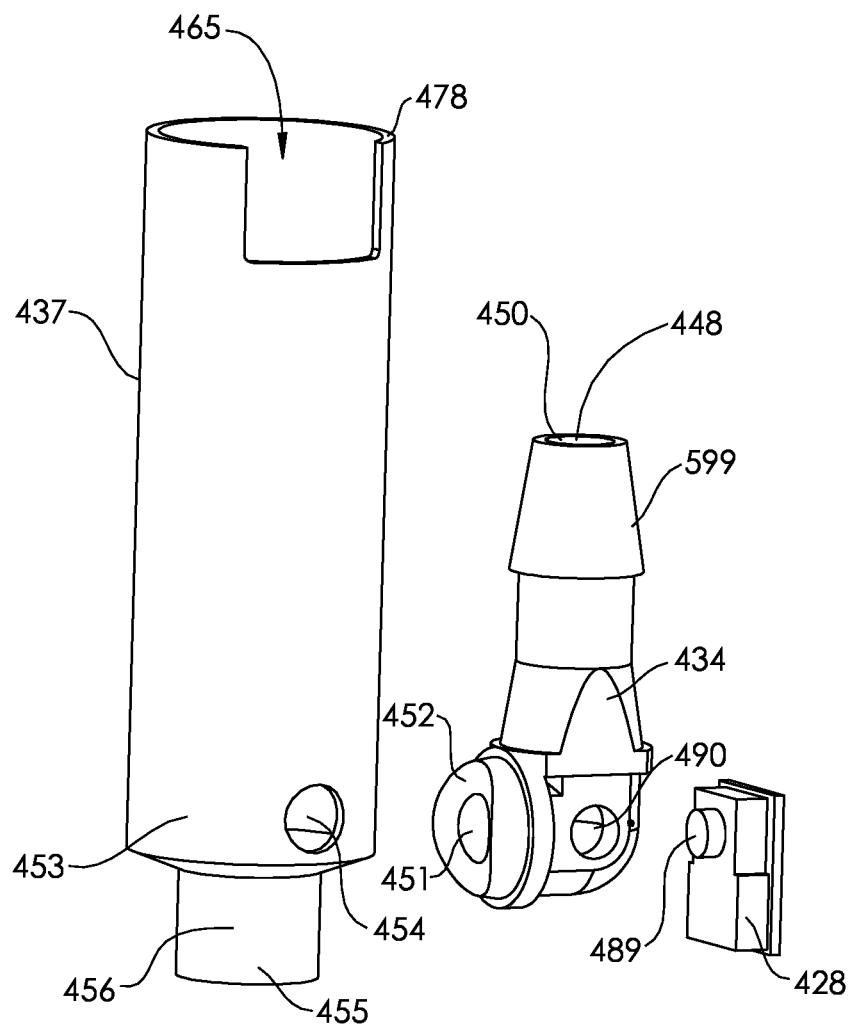
FIG. 10 is an exploded view of some internal components of the control.
Figure 11:
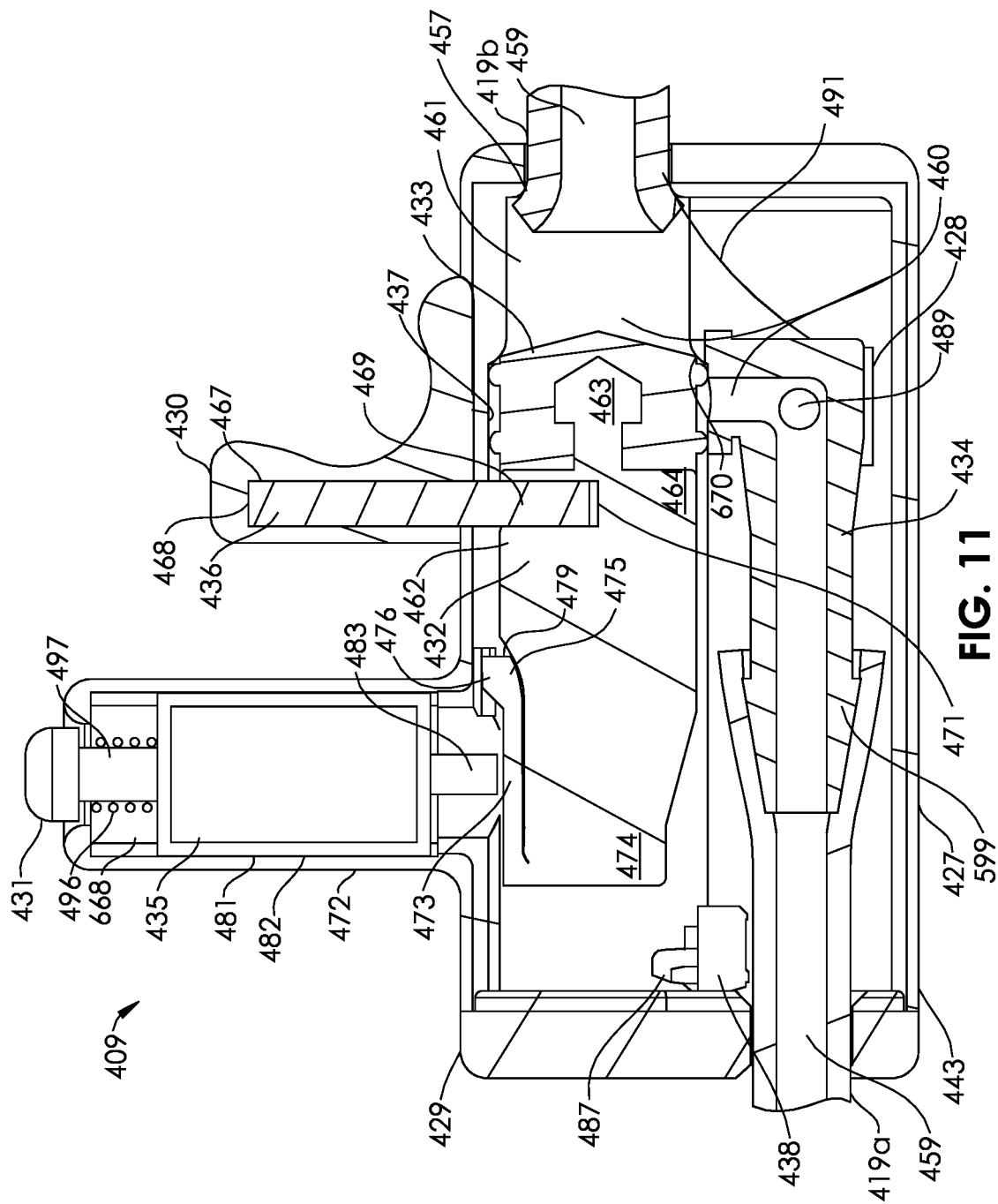
FIG. 11 is a sectional view of the control in a closed position, according to an embodiment of the present disclosure.

Referring to FIGS. 11-12, the S-duct 460 provides the interior space of a valve 461, via the sliding of a plunger 433 that is carried by a piston body 432, thus forming a piston 462 structure. The piston body 432 may comprise a rigid polymer, such as a polyamide. FIG. 11 illustrates the valve 461 in a closed position, stopping flow through the passageway 459, and FIG. 12 illustrates the valve 461 in an open position, allowing flow through the passageway 459. The plunger 433 is snapped onto a barb 463 at a first end 464 of the piston body 432, and is configured to move in unison with the piston body 432 within a cylindrical cavity 465 (FIG. 10) within the cylinder 437, the cylindrical cavity 465 (FIG. 10) having an internal volume. Alternatively, the plunger 433 may couple to the piston body 432 by screwing, clipping, friction fitting, or other manners. A slider 430 includes a concavity 466 for engaging the finger of a user and includes a hole 467 (FIGS. 11-12) into which a first end 468 of a spring pin 436 is frictionally engaged. Alternatively, the spring pin 436 may be bonded into the hole 467. The spring pin 436 is configured to be slidable, back-and-forth within an elongate slot 470 in the cylinder 437. The second end 469 of the spring pin 436 is frictionally engaged into a hole 471 in the piston body 432. The housing 443 includes a handle 472 extending transversely therefrom, and configured for holding or grasping (e.g., by the user's hand or one or more fingers) in opposition to the concavity 466 of the slider 430. Thus, by forcing the slider 430 to move relative to the housing 443 toward the handle 472, in the direction of the arrow 666 that is molded or otherwise marked on the side 669 of the first half 426, the piston body 432 is retracted, bringing the plunger 433 with it, and thus changing the valve 461 from the closed position of FIG. 11 to the open position of FIG. 12.

Figure 8:
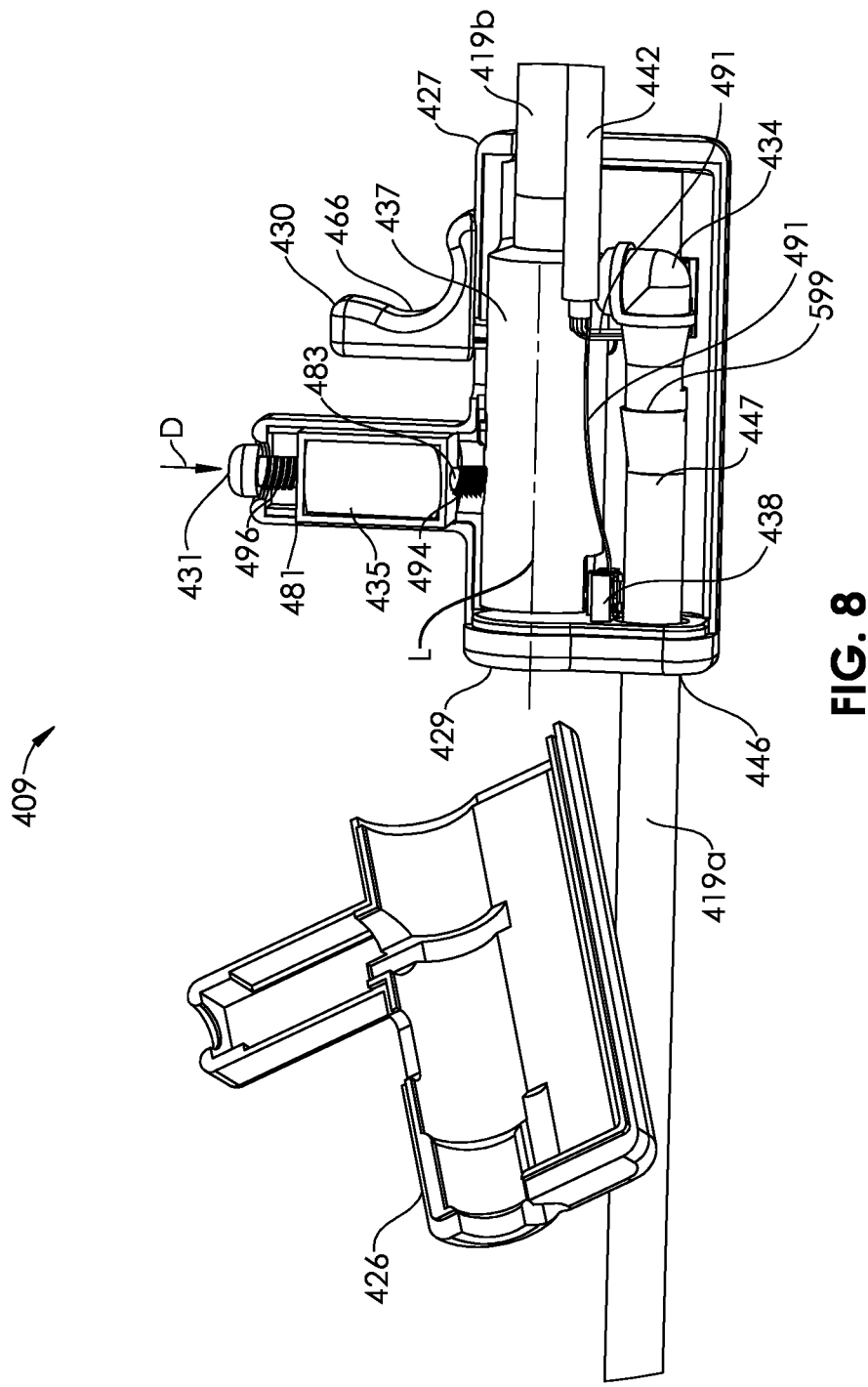
FIG. 8 is a view of the intern components of the control of FIG. 6.

The piston body 432 further includes a cantilever beam 473 extending longitudinally from a second end 474 of the piston body 432 and terminating in a free beam end 475 having a locking tab 476. When the valve 461 is in its open position, the locking tab 476 is configured to extend out through a locking hole 477 in the wall 478 of the cylinder 437. Because the valve 461 is open, the negative pressure within the passageway 459 sucks, and thus pulls, the plunger 433 (and thus, the piston body 432) in the opposite direction from the arrow 666 on the first half 426 of the housing 443. Thus, with features best seen in FIG. 9, an extreme edge 479 of the locking tab 476 stops against a distal ledge 480 of the locking hole 477, maintaining and locking the valve 461 in the open position. An unlocking assembly 481, comprising a casing 482 and a button 431, is slidable within a cavity 668 of the handle 472 in a direction generally transverse to longitudinal axis L of the cylinder 437/piston body 432 (FIG. 8). A user may voluntarily unlock the piston body 432 from the cylinder 437 by pressing the button 431 in direction D, causing an engagement pin 483 of the unlocking assembly 481 to push the locking tab 476 transversely inward (also generally in direction D) while causing the cantilever beam 473 to flex or deflect, thus moving the entirety of the locking tab 476 into the cylinder 437, fully free of the locking hole 477, and no longer engaged with the distal ledge 480. Therefore, the negative pressure within the passageway 459 is now able to cause the plunger 433 (and thus, the piston body 432) to move in the opposite direction from the arrow 666 such that the valve 461 forcibly closes. The plunger 433 being sealingly forced against an interior annular edge 670 at the end of the cylinder 437. In this closed position, the locking tab 476 is moved to a position adjacent a resting hole 484 (FIG. 9), and the spring memory of the cantilever beam 473 causes the locking tab 476 to move transversely (generally opposite direction D), and through the resting hole 484. The negative pressure within the passageway 459 forces the plunger 433/piston body 432, with some compression of the elastomeric plunger 433 material, such that the extreme edge 479 of the locking tab 476 is stopped against a resting ledge 485, thus freezing the piston body 432 in a single position with the valve 461 closed. Flow through the passageway 459 is thus interrupted. A compression spring 496 may be carried on a shaft 497 below the button 431 to cause the button 431 and the unlocking assembly 481 to return to the original position after the button 431 is depressed and then released.

An electrical switch 438 is carried within a groove 486 of the end cover 429 and includes a spring-loaded, displaceable switch button 487. When the valve 461 is opened, the piston body 432 is slid toward the switch 438 such that an annular edge 488 of the second end 474 of the piston body 432 engages and moves the switch button 487, thus activating the electrical switch 438. In some embodiments, the activation of the electrical switch 438 causes the pump of the SDU 411 to start injecting pressurized fluid through the supply lumen 2093 of the catheter 406. In some embodiments, the deactivation of the electrical switch 438 causes the pump of the SDU 411 to stop. The movement of the piston body toward the direction in which the valve 461 is closed causes the annular edge 488 to move away from and stop engaging the switch button 487, thus shutting off the switch. In some embodiments, the electrical switch 438 may comprise an SPST-NO switch. Thus, the opening and closing of the valve 461 and the turning on and off of the pump of the SDU 411 are synchronized together by a combination electric and hydraulic switch comprised by the control 409. In manual operation, a user opens the valve 461 and also turns on the pump of the SDU 411 by moving the slider 430. The user then closes the valve 461 and turns off the pump of the SDU 411 by pushing the button 431. The controller 493 is configured to receive the signal from the switch 438, and to turn the pump of the SDU 411 to start (or stop) immediately, or with a particular delay time.

An emergency shut-off is provided by a solenoid 435 within the unlocking assembly 481, and a pressure sensor 428 configured to measure the pressure within the passageway 459. Turning to FIG. 10, the pressure sensor 428 includes a sensing portion 489 which is inserted through a hole 490 in the elbow fitting 434. The surrounding portions of the pressure sensor 428 and the elbow fitting 434 are then sealed with epoxy, adhesive, or other means. Thus, the pressure sensor 428 is capable of measuring the pressure within inner passage 448 of the elbow fitting 434 and outputting a signal related to the measured parameter. Alternatively, the pressure sensor 428 (or another pressure sensor) can be configured to measure the pressure in another location along the passageway 459, or even in the aspiration lumen 2032 of the catheter 406. A wire conduit 442 extends in parallel along the suction tubing 419*b* and carries on or more or two or more conductors 491. The conductors 491 may each comprise insulated copper wire. The conductors 491 are configured to deliver power and/or to carry signals to and from the pressure sensor 428, the switch 438, and the solenoid 435, as well as the additional pressure sensor 604, if used. As mentioned, at the second end 458 of the tubing 419*b*, the conductors 491 terminate via electrical connection to a modular plug connector 439 that is configured to snap into the mating receptacle 492 in the SDU 411 (FIG. 4). The connector 439 may in some embodiments be an eight position, eight contact (8p8c) connector.

Figure 9:
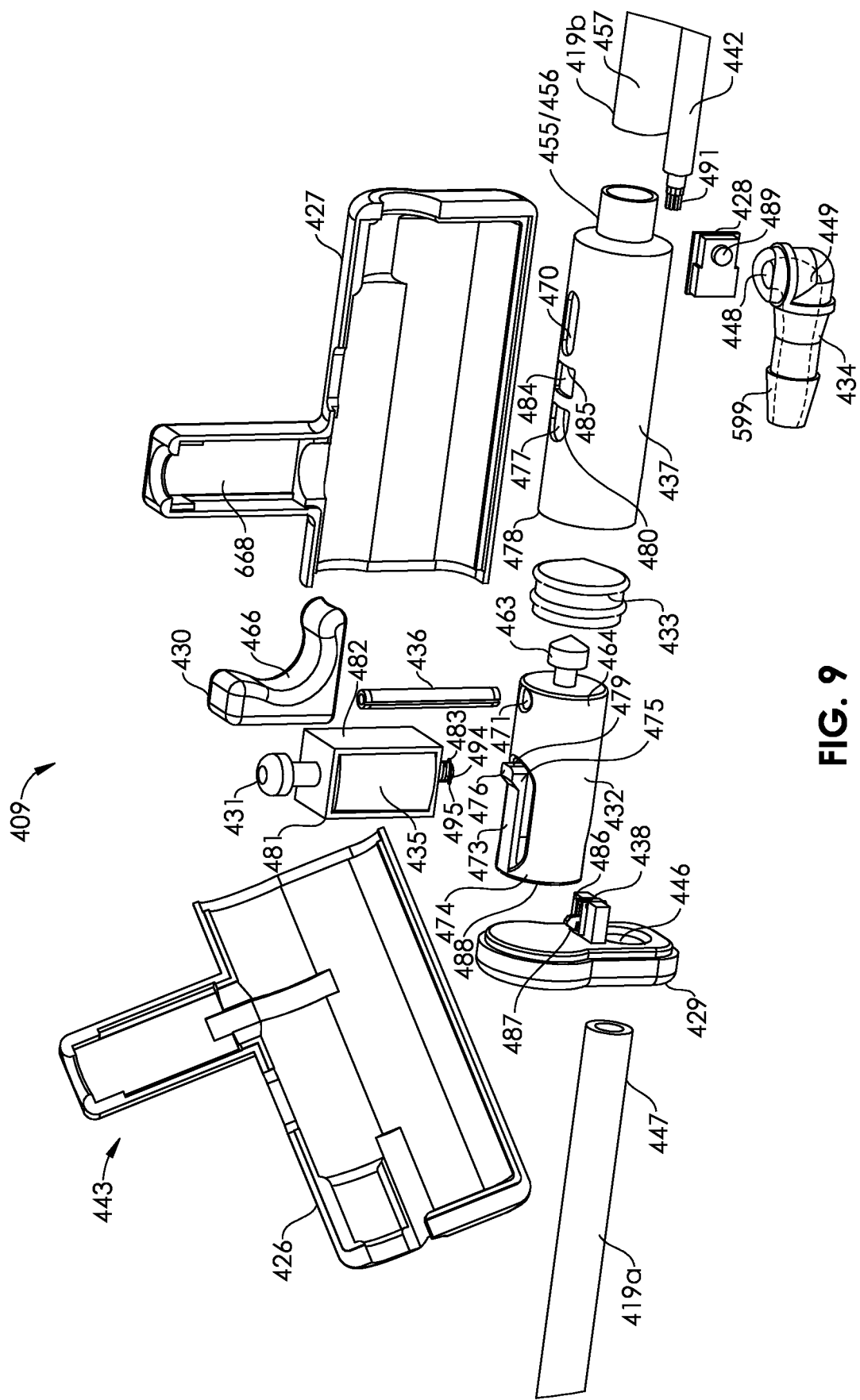
FIG. 9 is an exploded view of the control.

While the valve 461 is in the open position and the pump of the SDU 411 is operating (e.g., via the saddle 648), a malfunction may occur that causes a loss in negative pressure within the passageway 459. The user may not realize that this has happened, and thus the potentially hazardous situation of injecting the pressurized fluid without any aspiration may occur. The pressure sensor 428 inputs to the controller 493, which is configured to recognize when an unacceptable pressure is being read (e.g., insufficient level of vacuum). The controller 493 is configured to temporarily energize the solenoid 435, which causes the engagement pin 483 of the unlocking assembly 481 to telescopically extend from the solenoid 435, thus electromagnetically energizing the solenoid 435 to move the locking tab 476 transversely inward (direction D) while causing the cantilever beam 473 to flex, pushing the entirety of the locking tab 476 within the cylinder 437, free of the locking hole 477. This allows the valve 461 to close and the pump of the SDU 411 to be immediately shut off, avoiding the potentially hazardous situation. A spring 494 and retaining ring 495 are shown in FIG. 9 and are configured to return the engagement pin 483 to its unextended position, after the controller 493 stops energizing the solenoid 435. Other safety features related to system shut-down, or other automatic system responses, may be utilized, such as those described in U.S. Pat. No. 10,716,583, issued Jul. 21, 2020, and entitled, "Systems and Methods for Removal of Blood and Thrombotic Material", U.S. Pat. No. 10,492,805, issued Dec. 3, 2019, and entitled, "Systems and Methods for Thrombosis and Delivery of an Agent" or U.S. Pat. App. Pub. No. 2018/0207397, published Jul. 26, 2018, and entitled, "Systems and Methods for Removal of Blood and Thrombotic Material", all of which are incorporated by reference in their entirety for all purposes.

Returning to FIG. 5, a solenoid 672 is carried internally in the SDU 411, and is configured to interface with the interior 676 of the canister 407, via the suction tubing 408, or via any additional tubing. The solenoid 672 is configured to vent the negative pressure inside the canister 407, by opening a valve 674 coupled to the solenoid (mechanically or electromagnetically) that opens the interior 676 of the canister 407 to ambient pressure. The venting allows any foaming of blood or fluid, such as any aspirated liquid, within the canister 407 to be reduced. Foaming can occur during a thrombolysis procedure due to cavitation, as air bubbles are formed. The solenoid 672 is then configured to close the valve 674, to allow negative pressure to again be built up within the interior 676 of the canister 407. The controller 493 is configured to automatically energize the solenoid 672, in order to allow for the degassing/defoaming. For example, the controller 493 may send a signal to energize the solenoid 672 based on the measurement of a targeted negative pressure and/or a targeted time of aspiration cycle. In other cases, the controller 493 can send a signal to energize the solenoid 672 every minute, every five minutes, every ten minutes, etc. Additionally, a user can operate the controller 493, and more generally the controller 303, of the system 400 through the interface panel 662 to initiate degassing/defoaming of the interior 676. The venting may also be able to remove air bubbles inside the other lumens of the catheter and tubing sets.

In some embodiments, the controller 493 can output or send a signal to energize the solenoid 672 to open the valve 674, in order to stop any aspiration, while still allowing the SDU 411 to deliver saline, medication, or saline combined with medication (e.g., thrombolytic drugs), so that the fluids can be delivered out of the open distal end 2036 (instead of being aspirated through the aspiration lumen 2032).

Figure 13:
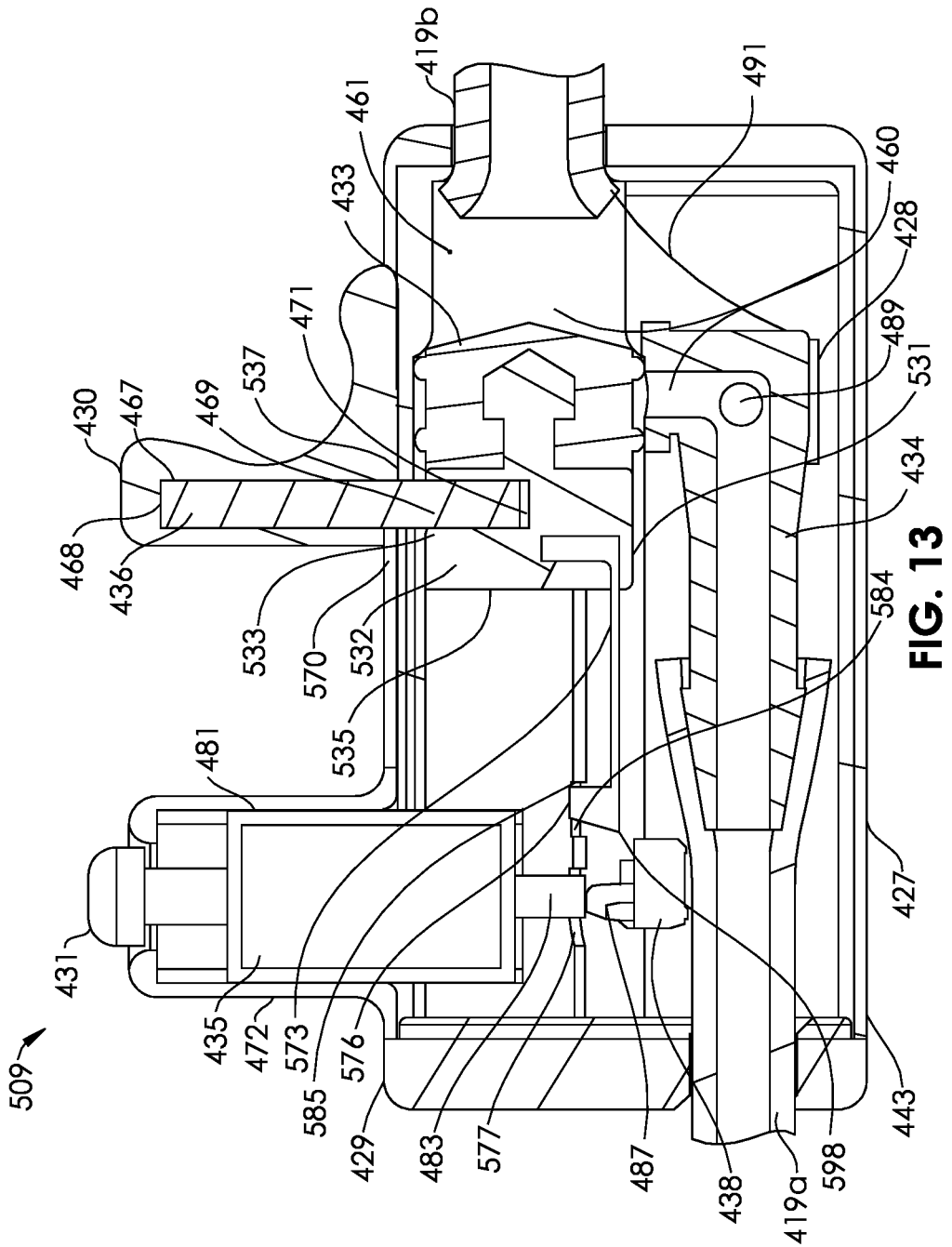
FIG. 13 is a sectional view of a control in a closed position, according to an alternative embodiment of the present disclosure.
Figure 14:
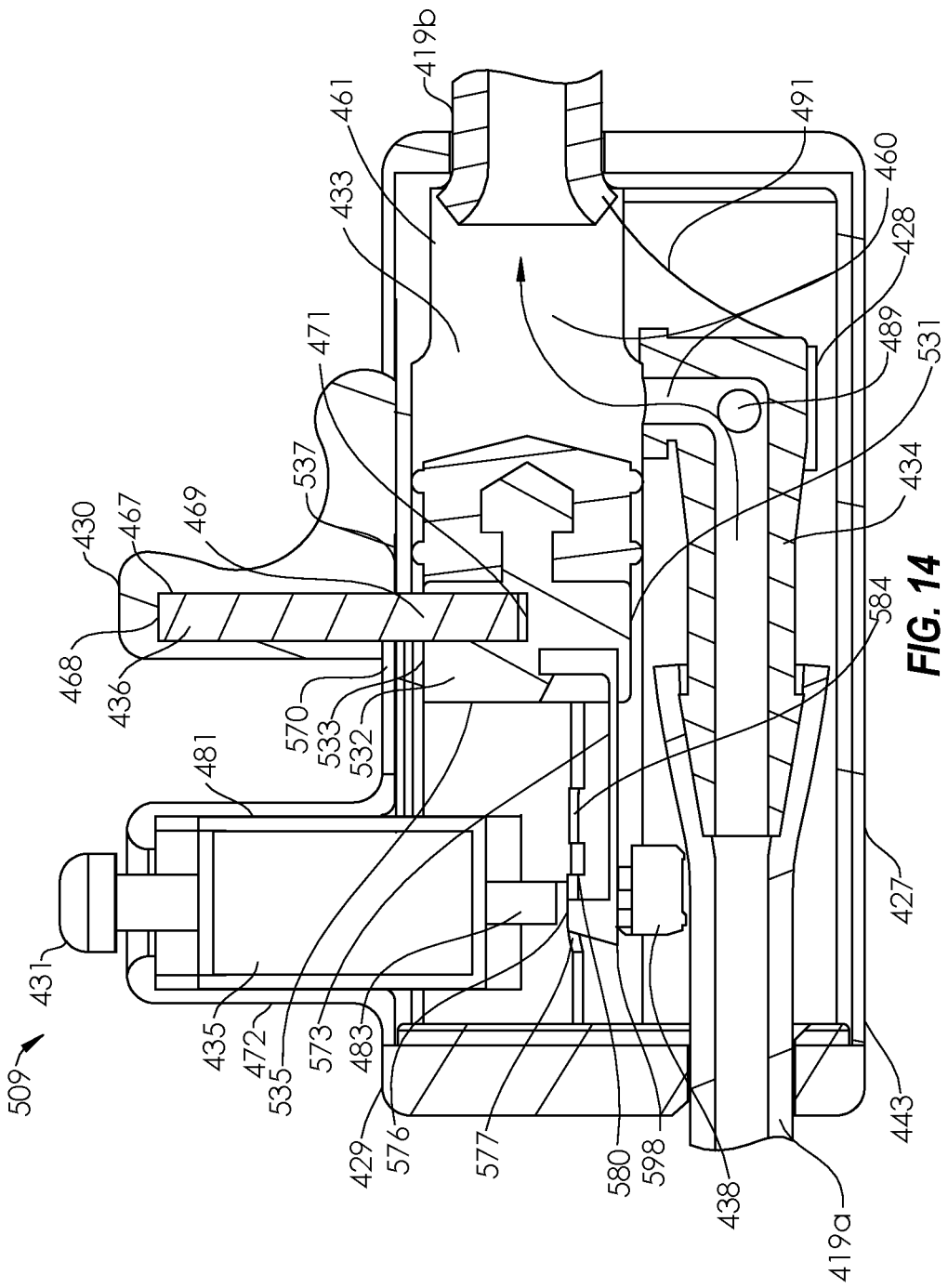
FIG. 14 is a sectional view of the control of FIG. 13 in an open position.

FIGS. 13-14 illustrate an alternative control 509 that generally contains the same components as the control 409, except for certain alternative or additional parts, including a modified piston body 532 and a modified cylinder 537. The cantilever beam 573 extends away from the plunger 433 instead of toward it. The cantilever beam 573 is also on an opposite (e.g., lower) side 531 of the cylinder 537 than the slider 430, which is on the upper side 533. The cantilever beam 573 is attached to the cylinder 537 at its proximal end 535. The resting hole 584 and resting ledge 585, as well as the locking hole 577 and the distal ledge 580, are on the opposite side 531 of the cylinder 537 than is the elongate slot 570, which is on the upper side 533. Note: that "upper" and "lower" are used in this case to denote opposites, and should not be considered to limit the manner in which the control 509 is intended to be held. It may be held in a number of orientations, depending upon the preference of the user. Whereas in the control 409, the annular edge 488 of the second end 474 of the piston body 432 engages and moves the switch button 487 and activates the electrical switch 438, in the control 509, the tip 598 of the locking tab 576 moves the switch button 487, when the piston body 432 is moved toward the switch 438. It should be noted that in either the control 409 or the control 509, instead of a cantilever beam 473, 573 having locking tabs 476, 576, any other structure or structures may be used that allows for locking and unlocking.

In a further alternative embodiment, the control 409 or control 509 may be configured to be foot-operated instead of hand-operated. Representative foot pedals for achieving this may also utilize features as described in U.S. Pat. App. Pub. No. 2018/0207397, published Jul. 26, 2018, and entitled, "Systems and Methods for Removal of Blood and Thrombotic Material".

Although the systems for aspirating thrombus described herein are predominantly focused on aspiration, the systems may also, or alternatively, be configured for injecting or infusing fluids, with or without drugs, and may incorporate related features described in U.S. Pat. No. 10,716,583, issued Jul. 21, 2020, and entitled, "Systems and Methods for Removal of Blood and Thrombotic Material" and U.S. Pat. No. 10,492,805, issued Dec. 3, 2019, and entitled, "Systems and Methods for Thrombosis and Delivery of an Agent".

It is contemplated that various combinations or subcombinations of the specific features and aspects of the embodiments disclosed above may be made and still fall within one or more of the embodiments. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed embodiments. Thus, it is intended that the scope of the present disclosure herein disclosed should not be limited by the particular disclosed embodiments described above. Moreover, while the present disclosure is susceptible to various modifications, and alternative forms, specific examples thereof have been shown in the drawings and are herein described in detail. It should be understood, however, that the present disclosure is not to be limited to the particular forms or methods disclosed, but to the contrary, the present disclosure is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

For purposes of the present disclosure and appended claims, the conjunction "or" is to be construed inclusively (e.g., "an apple or an orange" would be interpreted as "an apple, or an orange, or both"; e.g., "an apple, an orange, or an avocado" would be interpreted as "an apple, or an orange, or an avocado, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open-ended terminology, with the same meaning as if the phrase "at least" were appended after each instance thereof.

What is claimed is:

1. A system for aspirating thrombus, the system comprising:
   an aspiration catheter comprising a supply lumen and an aspiration lumen;
   a drive unit for pumping fluid through the supply lumen of the aspiration catheter;
   a support assembly to which the drive unit is mounted; and
   a combined hydraulic and electrical control in fluid communication with the aspiration lumen, the combined hydraulic and electrical control comprising:
   a control body configured to be moved between a first position and a second position, the control body comprises a piston having a first end and a second end, the piston configured to sealingly slide within a cylinder having an internal volume;
   a first control interface configured to be activated by a user to move the control body between the first position and the second position;
   an electrical switch configured to be activated by the control body when the control body is moved to the second position; and
   a valve having a closed position blocking flow from the aspiration lumen and an open position allowing flow from the aspiration lumen, the valve configured to be moved from the closed position to the open position by the control body when the control body is moved to the second position.

2. The system of claim 1, wherein the support assembly comprises a cart.

3. The system of claim 1, wherein the aspiration lumen is in fluid communication with a vacuum receptacle.

4. The system of claim 1, wherein the aspiration lumen communicates with a vacuum source and the supply lumen communicates with a fluid source.

5. The system of claim 1, wherein the drive unit comprise a pump to pump a pressurized fluid through the supply lumen.

6. The system of claim 5, wherein the electrical switch, when activated, is configured to cause the pump to pump the pressurized fluid.

7. The system of claim 5, wherein the electrical switch, when deactivated, is configured to stop the pump.

8. The system of claim 1, wherein the valve comprises a plunger carried on the first end of the piston.

9. The system of claim 8, wherein the control body is configured to be locked in the second position.

10. The system of claim 8, wherein the valve is configured to be pulled into the closed position by negative pressure within a passageway extending through the combined hydraulic and electrical control.

11. The system of claim 8, wherein the valve is configured to be pulled into the closed position when a first pressure within a passageway extending through the combined hydraulic and electrical control is less than a second pressure within a cylinder adjacent the second end of the piston.

12. The system of claim 11, further comprising a release control configured to unlock the control body to allow the control body to move away from the second position.

13. The system of claim 11, wherein, when the control body is unlocked, the valve is configured to be pulled into the closed position when a first pressure within the passageway is less than a second pressure within the cylinder adjacent the second end of the piston.

14. The system of claim 13, wherein the release control comprises a hand-operatable interface.

15. The system of claim 13, wherein the release control comprises a foot-operatable interface.

16. The system of claim 13, wherein the release control comprises a solenoid.

17. The system of claim 13, wherein the release control comprises an operator-contact-operated interface and a solenoid.

18. The system of claim 13, further comprising a locking tab associated with the control body and displaceable in a direction generally transverse to a longitudinal axis of the control body.

19. The system of claim 18, wherein the locking tab is coupled to the control body via a deflectable beam.

20. The system of claim 19, wherein the deflectable beam extends in a direction generally parallel to the longitudinal axis of the control body.

21. The system of claim 20, wherein the deflectable beam extends in a direction generally toward the valve.

22. The system of claim 20, wherein the deflectable beam extends in a direction generally away from the valve.

23. The system of claim 1, further comprising a pressure sensor configured to measure pressure within a passageway through the combined hydraulic and electrical control and output a signal related to the measured pressure.

24. The system of claim 23, further comprising a controller configured to receive the signal from the pressure sensor.

25. The system of claim 1, further comprising a flow sensor configured to measure a parameter related to fluid flow within a passageway through the combined hydraulic and electrical control and output a signal related to the measured parameter.

26. The system of claim 25, wherein an operator contact-operated interface and a solenoid are combined and configured such that the operator-contact-operated interface is configured for voluntary unlocking of the control body and such that the solenoid is configured for automatic unlocking of the control body.

27. The system of claim 26, wherein the solenoid is configured for emergency shut-off of the system.

* * * * *